(12) United States Patent
McGrath, Jr.

(10) Patent No.: US 11,717,698 B1
(45) Date of Patent: Aug. 8, 2023

(54) THERAPY, TREATMENT, AND PROCESS FOR PHOTODYNAMIC INACTIVATION OF COVID-19

(71) Applicant: Hugh McGrath, Jr., Covington, LA (US)

(72) Inventor: Hugh McGrath, Jr., Covington, LA (US)

(*) Notice: Subject to any disclaimer, the term of this patent is extended or adjusted under 35 U.S.C. 154(b) by 69 days.

(21) Appl. No.: 17/238,959

(22) Filed: Apr. 23, 2021

Related U.S. Application Data

(60) Provisional application No. 63/019,992, filed on May 4, 2020, provisional application No. 63/014,702, filed on Apr. 23, 2020.

(51) Int. Cl.
*A61N 5/06* (2006.01)

(52) U.S. Cl.
CPC ......... *A61N 5/0624* (2013.01); *A61N 5/0618* (2013.01); *A61N 2005/064* (2013.01); *A61N 2005/0654* (2013.01); *A61N 2005/0661* (2013.01); *A61N 2005/0667* (2013.01)

(58) Field of Classification Search
CPC ............... A61N 5/0624; A61N 5/0618; A61N 2005/064; A61N 2005/0654; A61N 2005/0661; A61N 2005/0667
See application file for complete search history.

(56) References Cited

U.S. PATENT DOCUMENTS

| | | | |
|---|---|---|---|
| 4,151,030 A | 4/1979 | Hensel | |
| 4,298,005 A | 11/1981 | Mutzhas | |
| 4,683,379 A | 7/1987 | Wolff | |
| 5,658,722 A | 8/1997 | Margolis-Nunno et al. | |
| 6,063,108 A | 5/2000 | Salansky et al. | |
| 6,537,304 B1 | 3/2003 | Oron | |
| 6,635,642 B1 | 10/2003 | Jackson et al. | |
| 6,902,563 B2 | 6/2005 | Wilkens et al. | |
| 7,041,343 B1 | 5/2006 | Nelles et al. | |
| 10,517,538 B2 | 12/2019 | Burnett et al. | |
| 2002/0155098 A1 | 10/2002 | Bolton et al. | |
| 2003/0202939 A1 | 10/2003 | Green | |
| 2004/0087485 A1 | 5/2004 | Iian et al. | |
| 2005/0197681 A1 | 9/2005 | Barolet et al. | |

(Continued)

OTHER PUBLICATIONS

Arno Wiehe, "Trends and targets in antiviral phototherapy" Photochem. Photobiol. Sci., 2019, 18, 2565-2612 (Year: 2019).*

(Continued)

*Primary Examiner* — Brian T Gedeon
*Assistant Examiner* — Joshua Andrew Schum-Houck
(74) *Attorney, Agent, or Firm* — Garvey, Smith & Nehrbass, Patent Attorneys, L.L.C.; Julia M. FitzPatrick; Vanessa M. D'Souza

(57) ABSTRACT

A therapy, treatment and process for inactivating and/or killing COVID-19 (Corona Virus Disease 2019) is provided, including a low-dose, full body, Ultraviolet A1 (UV-A1, 360-400 nm) photon therapy, wherein the UV-A1 photon therapy activates singlet oxygen ($^1O_2$), which inactivates and/or kills COVID-19. UV-A1 therapy of the present invention can also be used to help alleviate symptoms and secondary illnesses caused by COVID-19. UV-A1 therapy of the present invention can also be used to help alleviate and treat pre-existing conditions of people that are also suffering from COVID-19 and worsened by COVID-19.

20 Claims, 8 Drawing Sheets

(56) References Cited

U.S. PATENT DOCUMENTS

| | | | |
|---|---|---|---|
| 2006/0184214 A1 | 8/2006 | McDaniel | |
| 2007/0179570 A1 | 8/2007 | DeTaboada et al. | |
| 2007/0255266 A1* | 11/2007 | Cumbie | A61N 5/0624 606/9 |
| 2010/0121420 A1* | 5/2010 | Fiset | A61N 5/06 607/94 |
| 2020/0101313 A1* | 4/2020 | Morita | A61N 5/0616 |

OTHER PUBLICATIONS

Fekrazad R. Photobiomodulation and Antiviral Photodynamic Therapy as a Possible Novel Approach in COVID-19 Management. Photobiomodul Photomed Laser Surg. May 2020;38(5):255-257. doi: 10.1089/photob.2020.4868. Epub Apr. 23, 2020. PMID: 32326830. (Year: 2020).*

M. C. A. Polderman, S. le Cessie, T. W. J. Huizinga. S. Pavel, Efficacy of UVA-1 cold light as an adjuvant therapy for systemic lupus erythematosus, Rheumatology 2004; 43:1402-1404, Advance Access publication (Aug. 10, 2004).

H McGrath Jr., Elimination of anticardiolipin antibodies and cessation of cognitive decline in a UV-AI-irradiated systemic lupus erythematosus patient, Lupus (2005) 14, 859-861.

H McGrath Jr., Elimination of anticardiolipin antibodies and cessation of cognitive decline in a UV-AI-irradiated systemic lupus erythematosus patient, Lupus (2005) 14 I-3.

Benjamin Jabara, MD: Mollie Dahlgren, MD: and Hugh McGrath, Jr., MD, Interstitial Lung Disease and Pulmonary Hypertension Responsive to Low Dose UVA1 Irradiation in Lupus, PMC Jun. 1, 2011.

Benjamin Jabara, MD: Mollie Dahlgren, MD, and Hugh McGrath, Jr., MD. Interstitial Lung Disease and Pulmonary Hypertension Responsive to Low-Dose UVA1 Irradiation in Lupus, PMC Jun. 2, 2010.

S. Pavel, Light therapy (with UV A-1) for SLE patients: is it a good or bad idea?, Rheumatology (Jun. 2006) 45 (6): 653-655 (First published online: Mar. 7, 2006).

Jose F. Molina and Hugh McGrath Jr., Longterm Ultraviolet-AI Irradiation Therapy in Systemic Lupus Erythematosus, The Journal of Rheumatology 1997; 24:6, 1072-1074.

Hugh McGrath Jr., Prospects for UV-A1 therapy as a treatment modality in cutaneous and systemic LE, Lupus (1997)6, 209-2: 7.

Y Menon, K McCarthy and H McGrath Jr., Reversal of brain dysfunction with UV-AI irradiation in a patient with systemic lupus, Lupus (2003) 12, 479-482.

MC A Polderman, C van Kooten, NP M Smit, SW A Kamerling, Ultraviolet-A (UV A-1) radiation suppresses immunoglobuli activated B lymphocytes in vitro, Clin Exp Immunol. Sep. 1, 2006; 145(3): 528-534.

H McGrath, Jr., Ultraviolet-A1 irradiation therapy for systemic lupus erythematosus, LUPUS, Oct. 2017; 26(12): 1239-1251 (Published online May 8, 2017).

A. Szegedi, E. Simics, M. Aleksza, I. Horkay, K. Gaal, S. Sipka, J. Hunyadi and E. Kiss, UltravioletrAI phototherapy modulates Th1/Th2 and Tc1/Tc2 balance in patients with systemic/lupus erythematosus, Rheumatology 2005,44 :925-931, Advance Access publication, Apr. 12, 2005.

Hugh McGrath, Jr., Ultraviolet A1 (340-400 nm) Irradiation and Systemic Lupus Erythematosus, 1087-0024/99, Copyright © 1999, bv The Society for Investigative Dermatology, Inc., vol. 4, No. 1 Sep. 1999.

M. Lindenblatt, R. Bordel, W. Schareck, M.D. Menger, B. Vollmar, Vascular Heme Oxygenase-1 Induction Suppresses Microvascular Thrombus Formation In Vivo, Arterioscler Thromb Vase Biol Mar. 2004; 24(3): 601-6 doi: 10.1161/01.ATV.0000118279.74056.8a. Epub Jan. 22, 2004.

Helen Christou, Toshisuke Morita, Chung-Ming Hsieh, Hideo Koike, Burak Arkonac, Mark A. Perella, Stella Kourembanas, Prevention of Hypoxia-Induced Pulmonary Hypertension by Enhancement of Endogenous Heme Oxygenase-1 in the Rat, Jun. 23, 2000 https://doi.org/10.1161/01.RES.86.12.1224Circulation Research. 2000; 86:1224-1229.

Soraia Genebra Ibrahim Forgiarini, Darian Pase da Rosa, Luiz Felipe Forgiarini, Cassiano Teixeira, Cristiano Feijo Andrade, Luiz Alberto Forgiarini Junior, Elaine Aparecida Felix, Gilberto Friedman, Evaluation of systemic inflammation in patients being weaned from mechanical ventilation, Clinics (Sao Paulo). 2018;73:e256 doi: 10.6061/clinics/2018/e256. Epub Jun. 18, 2018.

Marcel Levi, Tymen T. Keller, Eric van Gorp, Hugo ten Cate, Infection and inflammation and the coagulation system, Cardiovasc Res. Oct. 15, 2003;60(1):26-39. doi: 10.1016/s0008-6363(02)00857-x.

Dean R. Hess PhD RRT FAARC, Inhaled Carbon Monoxide: From Toxin to Therapy, Respir Care. Oct. 2017;62 (10):1333-1342. doi: 10.4187/respcare.05781. Epub Aug. 14, 2017.

Mexander Hoetzel, Tama Dolinay, Simone Vallbracht, Yingze Zhang, Hong Pyo Kim, Emeka Ifedigbo, Sean Alber, A. Murat Kaynar, Rene Schmidt, Stefan W. Ryter, and Augustine M.K. Choi, Carbon Monoxide Protects against Ventilator-induced Lung Injury via PPAR-v and Inhibition of Egr-1, Am J Respir Crit Care Med. Jun. 1, 2008; 177(11): 1223-1232. Published online Mar. 20, 2008. doi: 10.1164/rccm.200708-1265OC.

Laura E. Fredenburgh, Mark A. Perrella, S. Alex Mitsialis, Heme Oxygenase-1: a Multifaceted Triple-Treat Molecule, Am J Respir Cell Mol Biol. Feb. 2007;36(2):137. doi: 10.1165/rcmb.2006-0002ED.

Shannon A. Bainbridge, Graeme N. Smith, HO in pregnancy, Free Radic Biol Med. Apr. 15, 2005;38(8):979-88. doi: 10.1016/j.freeradbiomed.2004.11.002.

Angela Tewari, Mette M.L. Grage, Graham L. Harrison, Robert Sarkany, Antony R. Young, UVA1 is skin deep: molecular and clinical implication, Photochemical & Photobiological Sciences, RSC Publishing, Photocohem. Photobiol. Sci, 2013, 12, 95. DOI 10.1039/c2pp25323b, www.rsc.org/pps.

Maria L. Zenclussen, Nadja Linzke, Anne Schumacher, Stefan Fest, Nicole Meyer, Pablo A. Casalis, Ana C. Zenclussen, Heme oxygenase-1 is critically involved in placentation, spiral artery remodeling, and blood pressure regulation during murine pregnancy, Front Pharmacol. 2014; 5: 291. Published online Jan. 13, 2015. doi: 10.3389/fphar.2014.00291.

Brian S. Zuckerbraun, Beek Yoke Chin, Barbara Wegiel, Timothy R. Billiar, Eva Czsimadia, Jayashree Rao, Larissa Shimoda, Emeka Ifedigbo, Shin Kanno, Leo E. Otterbein, Carbon monoxide reverses established pulmonary hypertension, JEM Copyright © The Rockerfeller University Press, vol. 203, No. 9, Sep. 4, 2006, 2109-2119, www.jem.org/cgi/doi/10.1084/jem.20052267.

Fabian Kasermanna Chritoph Kempf ab, Photodynamic inaction of enveloped viruses by buckminsterfullerene, Antiviral Res Mar. 1997;34(1):65-70. doi: 10.1016/s0166-3542(96)01207-7.

A. Szegedi, E. Simics, M. Aleksza, I. Horkay, K. Gaal, S. Sipka, J. Hunyadi, E. Kiss, Ultraviolet-A1 phototherapy modulates Th1/Th2 and Tc1/Tc2 balance in patients with systemic lupus erythematosus, Rheumatology 2005; 44:925-931, Advance Access publication Apr. 12, 2005, doi:10:1093/rheumatology/keh643.

Edyta Krzych-Falta, Dominika Modzelewska, Boleslaw Samolinski, Levels of exhaled carbon monoxide in healthy active and passive smokers, Przegl Lek. 2015;72(3):99-102.

Meggan Mackay, Lupus brain fog: a biologic perspective on cognitive impairment, depression, and fatigue in systemic lupus erythematosus,Immunol Res. Dec. 2015;63(1-3):26-37. doi: 10.1007/s12026-015-8716-3.

Konstanze Muller-Breitkreutz, Harold Mohr, Karlis Briviba, Helmut Sies, Inactivation of viruses by chemically and photochemically generated singlet molecular oxygen, Journal of Photochemistry and Photobiology B: Biology, vol. 30, Issue 1, Sep. 1995, pp. 63-70, https://doi.org/10.1016/1011-1344(95)07150-Z.

Karl A. Nath, Joseph P. Grande, John D. Belcher, Vesna D. Garovic, Anthony J. Croatt, Matthew L. Hillestad, Michael A. Barry, Meryl C. Nath, Raymond F. Regan, Gregory M. Vercellotti, Antithrombotic effects of heme-degrading and heme-binding proteins, Am J Physiol Heart Circ Physiol. Mar. 1, 2020; 318(3):H671-H681. Published

(56) References Cited

OTHER PUBLICATIONS online Jan. 31, 2020. doi: 10.1152/ajpheart.00280.2019:10.1152/ajpheart.02280.2019 Integrative Cardiovascular Physiology and Pathophysiology.
Susan Elmore, Apoptosis: a Review of Programmed Cell Death, Toxicol Pathol. Author manuscript; available in PMC Dec. 6, 2007. Published in final edited form as:Toxicol Pathol. 2007; 35(4): 495-516. doi:10.1080/01926230701320337.
Alexander Hoetzel, MD, Rene Schmidt, MD, Simone Vallbracht, PhD, Ulrich Goebel, M.D., Tamas Dolinay, MD, Hong Pyo Kim, PhD, Emeka Ifedigbo, Stefan W. Ryter, PhD, Augustine M.K. Choi, MD, Carbon monoxide prevents ventilator induced lung injury via caveolin-1, Crit Care Med. Author manuscript; available in PMC May 3, 2011. Published in final edited form as: Crit Care Med. May 2009; 37(5): 1708-1715. doi: 10.1097/CCM.0b013e31819efa31.
I Hamming, W Timens, MLC Bultuis, AT Lely, GJ Navis, H vanGoor, Tissue distribution of ACE2 protein, the functional receptor for SARS coronavirus. A first step in understanding SARS pathogenesis, Journal of Pathology, J Patol 2004; 203: 631-637, Published online in Wiley InterScience (www.interscience.wiley.com). DOI: 10.1002/path.1570.
Lin Peng, Fay William, [Heme oxygenase-1 inhibits thrombosis under oxidative stress], Zhonghua Xue Ye Xue Za Zhi. Nov. 2005; 26 (11):665-8.
Markus Grewe, Karin Gyufko, Jean Krutmann, Interleukin-10 Production by Cultured Human Keratinocytes: Regulation by Ultraviolet B and Ultraviolet A1 Radiation, J Invest Dermatol.Jan. 1995; 104(1):3-6. doi: 10.1111/1523-1747. ep12613446.
Dianne E. Godar, Light and Death: Photon and Apoptosis, J Investig Dermatol Symp Proc. Sep. 1999;4(1):17-23. doi: 10.1038/sj.jidsp. 5640175.
R. Tyrrell, Redox regulation and oxidant activation of heme oxygenase-1, Free Radical Research vol. 31, 1999—Issue 4, pp. 335-340, Received Mar. 17, 1999, Published online: Jul. 7, 2009, doi.org/10.1080/10715769900300901.
E Reif, [What contributions offer the individual technics of pulmonary function tests to the clinical assessor for the evaluation of occupational diseases. II], Zentralbl Arbeitsmed. Nov. 16, 1967; 17(11):336-44.
Dianne E. Godar, Preprogrammed and Programmed Cell Death Mechanisms of Apoptosis: UV-Induced Immediate and Delayed Apoptosis, Photochem Photobiol.Jun. 1996;63(6):825-30.doi: 10.1111/j.1751-1097.1996.tb09638.x.
Soodabeh Zandi, Sunil Kalia, Harvey Lui, UVA1 phototherapy: a concise and practical review, Skin Therapy Lett Jan. 2012;17(1):1-4.
Nathan R. York BS, Heidi T. Jacobe MD, MSCS, UVA1 phototherapy: a review of mechanism and therapeutic application, International Journal of Dermatology/vol. 49, Issue 6/p. 623-630, doi.org/10.1111/j.1365-4632.2009.04427.x.
J. Baier, Tim Maisch, Max Maier, Eva Engel, Michael Landthaler, Wolfgang Baumler, Singlet oxygen generation by UVA light exposure of engogenous photosensitizers, Aug. 15, 2006;91(4):1452-9. doi: 10.1529/biophysj.106.082388. Epub Jun. 2, 2006.
Mauricio S. Baptista, Jean Cadet, Paolo DiMascio, Ashwini A. Ghogare, Alexander Greer, Michael R. Hamblin, Carolina Lorente, Silvia Cristina Nunez, Martha Simoes Ribeiro, Andres H. Thomas, Mariana Vignoni, Tania Mateus Yoshimura, Type I and Type II Photosensitized oxidation Reactions: Guidelines and Mechanistic Pathways, Photochem Photobiol. Jul. 2017;93(4):912-919. doi:10.1111/php.12716. EpubMar. 27, 2017.
John A. Belperio, Michael P. Keane, Joseph P. Lynch 3rd, Robert M. Strieter, The role of cytokines during the pathogenesis of ventilator-associated and ventilator-induced lung injury. Semin Respir Crit Care Med. Aug. 2006;27(4):350-64. doi: 10.1055/s-2006-948289.
Yih Harng Chong, Nicola A. Dennis, Martin J. Connolly, Ruth Teh, Gregory T. Jones, Andre M. van Rij, Stephanie Farrand, A. John Campbell, Ian S. McLennan, Elderly men have low levels of anti-Mullerian hormone and inhibin B, but with high interpersonal variation: a cross-sectional study of the sertoli cell hormones in 615 commuity-dwelling men. PLoS One Aug. 5, 2013;8(8):e70967.doi: 10.1371/journal.pone.0070967. Print 2013.
Edström, D. W., Porwit, A., & Ros, A. M. (2001). Effects on human skin of repetitive ultraviolet-A1 (UVA1) irradiation and visible light. Photodermatol Photoimmunol Photomed, 17(2), 66-70. doi:10.1034/j.1600-0781.2001,017002066.x.
Y. Fang, F. Gao, Z. Liu, Angiotensin-converting enzyme 2 attenuates inflammatory response and oxidative stress in hyperoxic lung injury by regulating NF-KB and Nrf2 pathways. QJMDec. 1, 2019;112(12):914-924. doi: 10.1093/qjmed/hcz206.
Laura E. Fredenburgh, Mark A. Perrella, S. Alex Mitsialis, The Role of Heme Oxygenase-1 in Pulmonary Disease. Am J Respir Cell Mol Biol. Feb. 2007; 36(2): 158-165. Published online Sep. 15, 2006. doi: 10.1165/rcmb.2006-0331TR.
D.E. Godar, UVA1 radiation triggers two different apoptotic pathways. J Invest Dermatol.Jan. 1999;112(1):3-12. doi: 10 1046/j.1523-1747.1999.00474.x.
Chien-Ming Hu, Yen-Hui Chen, Ming-Tsai Chiang, Lee-Young Chau, Heme Oxygenase-1 Inhibits Angiotensin II-Induced Cardiac Hypertrophy In Vitro and In Vivo, Jun. 28, 2004 https://.org/10.1161/01.CIR.0000135475.35758.23Circulation. 2004; 110:309-316.
F. Kasermann, C. Kempf, Inactivation of enveloped viruses by singlet oxygen thermally generated from a polymeric naphthalene derivative, Antiviral Res. Apr. 1998;38(1):55-62. doi: 10.1016/s0166-3542(98)00007-2.
Roberto Motterlini, Brian E. Mann, Roberta Foresti, Therapeutic applications of carbon monoxide-releasing molecules, Expert Opin Investig Drugs. Nov. 2005;14(11):1305-18.
Firzan Nainu, Akiko Shiratsuchi, Yoshinobu Nakanishi, Induction of Apoptosis and Subsquent Phagocytosis of Virus-Infected Cells as an Antiviral Mechanism, Front Immunol. Sep. 28, 2017;8:1220. doi: 10.3389/fimmu.2017.01220. eCollection 2017.
Jari Petaja, Inflammation and coagulation. An overview. Thromb Res. Jan. 2011;127 Suppl 2:S34-7. doi: 10.1016/S0049-3848(10)70153-5.
Bruna G.G. Pinto, Antonio E.R. Oliveira, Youvika Singh, Leandro Jimenez, Andre N A. Goncalves, Rodrigo L.T. Ogava, Rachel Creighton, Jean Pierre Schatzmann Peron, Helder I. Nakaya, ACE2 Expression is Increased in the Lungs of Patients with Comorbidities Associated with Severe COVID-19, medRxiv PMC7276054, medRxiv. Preprint. Mar. 27, 2020. doi: 10.1101/2020.03.21.20040261.
M. Polderman, T. Huizinga, S. LeCessie, S. Pavel, UVA-1 cold light treatment of SLE: a double blind, placebo controlled crossover trial, Ann Rheum Dis. Feb. 2001; 60(2): 112-115. doi: 10.1136/ard.60.2.112.
Stefan W. Ryter, Augustine M.K. Choi, Cytoprotective and anti-inflammatory actions of carbon monoxide in organ injury and sepsis models, Novartis Found Symp. 2007;280:165-75; discussion 175-81.
Angela Tewari, Mette M.L. Grage, Graham I. Harrison, Robert Sarkany, Antony R. Young, UVA1 is skin deep. molecular and clinical implications. Photochem Photobiol Sci. Jan. 2013;12(1):95-103. doi: 10.1039/c2pp25323b. PMID: 23192740 DOI: 10.1039/c2pp25323b.
Bechet, D., Couleaud, P., Frochot, C., Viriot, M. L., Guillemin, F., & Barberi-Heyob, M. (2008). Nanoparticles as vehicles for delivery of photodynamic therapy agents. Trends Biotechnol, 26(11), 612-621. doi:10.1016/j.tibtech.2008.07.007.
Liliana Costa, Maria Amparo F. Faustino, Maria Graça P. M. S. Neves, Ângela Cunha and Adelaide Almeida, Photodynamic inactivation of Mammalian viruses and bacteriophages. Viruses. 2012; 4(7):1034-74.
McGrath H Jr, Martinez-Osuna P, Lee FA. Ultraviolet-A1 (340-400 nm) irradiation therapy in systemic lupus erythematosus. Lupus; 1996,5,269-274.
McGrath H Jr, Ultraviolet-A1 irradiation therapy for systemic lupus erythematosus. Lupus. 2017, 26(12);1239-1251.
Ibanez FJ, Farias MA, Retamal-Diaz A, et al. Pharmacological induction of heme oxygenase-1 impairs nuclear accumulation of Herpes Simplex virus capsids upon infection. Front Microbiol. 2017;8:2108.

(56) References Cited

OTHER PUBLICATIONS

Espinoza JA, Gonzalez PA, Kalergis AM. Am J Pathol. 2017. Modulation of antiviral immunity by heme oxygenase-1. 2017;187(3): 487-493.
Santangelo, R, Mancuso C, Marchetti s, et al. Bilirubin: an endogenous molecule with antiviral activity in vitro. Front Pharmacol. 2012, 3: 36.
Zhang A, Zhao L, Lin N, et al. Carbon monoxide inhibits porcine reproductive and respiratory syndrome virus replication by the cyclic GMP/protein kinase G and NF-kb signaling pathway. J Virol, 2017, 91.
McGrath H, Jr., Bak E, Michalski JP. Ultraviolet-A light prolongs survival and improves immune function in (New Zealand black x New Zealand white)F1 hybrid mice. Arthritis and rheumatism. 1987;30(5):557-561.
Jürgen Baier, Tim Maisch, Max Maier, Michael Landthaler, Wolfgang Bäumler. Direct detection of singlet oxygen generated by UVA irradiation in human cells and skin J Invest Dermatol. Jun. 2007;127(6):1498-506. doi: 10.1038/sj.jid.5700741. Epub Mar. 15, 2007.
Mutzhas MF, Holzle E, Hofmann C, Plewig G. A new apparatus with high radiation energy between 320-460 nm: physical description and dermatological applications. The Journal of investigative dermatology. 1981;76(1):42-47.
Tuchinda C, Kerr HA, Taylor CR, et al. UVA1 phototherapy for cutaneous diseases: an experience of 92 cases in the United States. Photodermatology, photoimmunology & photomedicine. 2006;22(5):247-253.
Morita A, Werfel T, Stege H, et al. Evidence that singlet oxygen-induced human T helper cell apoptosis is the basic mechanism of ultraviolet-A radiation phototherapy. The Journal of experimental medicine. 1997;186(10):1763-1768.
Tyrrell RM. Solar ultraviolet A radiation: an oxidizing skin carcinogen that activates heme oxygenase-1. Antioxidants & redox signaling. 2004;6(5):835-840.
Stief TW. The physiology and pharmacology of singlet oxygen. Medical hypotheses. 2003;60(4):567-572.
Kanofsky JR. Singlet oxygen production by biological systems. Chemico-biological interactions. 1989;70(1-2):1-28.
Graindorge D, Martineau S, Machon C, et al. Singlet Oxygen-Mediated Oxidation during UVA Radiation Alters the Dynamic of Genomic DNA Replication. PloS one. 2015;10(1371).
Ariela Benigni, Paola Cassis, Giuseppe Remuzzi. Angiotensin II revisited: new roles in inflammation, immunology and aging. EMBO Mol Med. Jul. 2010;2(7):247-57.
Debartolo A. Lupus Underground Evanston, II: Hyde Park Media 2004.
Chung SW, Liu X, Macias AA, Baron RM, Perrella MA. Heme oxygenase-1-derived carbon monoxide enhances the host defense response to microbial sepsis in mice. The Journal of clinical investigation. 2008;118(1):239-247.
Wegiel B, Hedblom A, Li M, et al. Heme oxygenase-1 derived carbon monoxide permits maturation of myeloid cells. Cell death & disease. 2014;5: e1139.
Alonso JR, Cardellach F, Lopez S, Casademont J, Miro O. Carbon monoxide specifically inhibits cytochrome c oxidase of human mitochondrial respiratory chain. Pharmacology & toxicology. 2003;93(3):142-146.
Ryter SW, Alam J, Choi AM. Heme oxygenase-1/carbon monoxide: from basic science to therapeutic applications. Physiological reviews. 2006;86(2):583-650.
Hanafy KA, Oh J, Otterbein LE. Carbon Monoxide and the brain: Time to rethink the dogma. Current Pharmaceutical Design 2013;19(15):2771-2775.
Kocer G, Nasircilar Ulker S, Senturk UK. The contribution of carbon monoxide to vascular tonus. Microcirculation (New York, NY: 1994). 2018;25(7): e12495.
Silva G, Cunha A, Gregoire IP, Seldon MP, Soares MP. The antiapoptotic effect of heme oxygenase-1 in endothelial cells involves the degradation of p38 alpha MAPK isoform. Journal of immunology (Baltimore, Md: 1950). 2006;177(3):1894-1903.
Durante W. Protective role of heme oxygenase-1 against inflammation in atherosclerosis. Frontiers in bioscience (Landmark edition). 2011; 16:2372-2388.
Sammut IA, Foresti R, Clark JE, et al. Carbon monoxide is a major contributor to the regulation of vascular tone in aortas expressing high levels of haeme oxygenase-1. British journal of pharmacology. 1998;125(7):1437-1444.
Motterlini R, Gonzales A, Foresti R, Clark JE, Green CJ, Winslow RM. Heme oxygenase-1-derived carbon monoxide contributes to the suppression of acute hypertensive responses in vivo. Circulation research. 1998;83(5):568-577.
Choi S, Kim J, Kim JH, et al. Carbon monoxide prevents TNF-alpha-induced eNOS downregulation by inhibiting NF-kappaB-responsive miR-155-5p biogenesis. Experimental & molecular medicine. 2017;49(11): e403.
Loboda A, Jazwa A, Grochot-Przeczek A, et al. Heme oxygenase-1 and the vascular bed: from molecular mechanisms to therapeutic opportunities. Antioxidants & redox signaling. 2008;10(10):1767-1812.
Dulak J, Jozkowicz A, Foresti R, et al. Heme oxygenase activity modulates vascular endothelial growth factor synthesis in vascular smooth muscle cells. Antioxidants & redox signaling. 2002;4(2):229-240.
Hettiarachchi NT, Boyle JP, Dallas ML, Al-Owais MM, Scragg JL, Peers C. Heme oxygenase-1 derived carbon monoxide suppresses Abeta1-42 toxicity in astrocytes. Cell death & disease. 2017;8(6): e2884.
Kurucz A, Bombicz M, Kiss R, et al. Heme Oxygenase-1 Activity as a Correlate to Exercise-Mediated Amelioration of Cognitive Decline and Neuropathological Alterations in an Aging Rat Model of Dementia. BioMed research international. 2018;2018:7212861.
Cass SP. Alzheimer's Disease and Exercise: a Literature Review. Current sports medicine reports. 2017;16(1):19-22.
Wang Y, Chai Y, He X, et al. Intermittent hypoxia simulating obstructive sleep apnea causes pulmonary inflammation and activates the Nrf2/HO-1 pathway. Experimental and therapeutic medicine. 2017;14(4):3463-3470.
Potue P, Wunpathe C, Maneesai P, Kukongviriyapan U, Prachaney P, Pakdeechote P. Nobiletin alleviates vascular alterations through modulation of Nrf-2/HO-1 and MMP pathways in l-NAME induced hypertensive rats. Food & function. 2019.
Daenen KE, Martens P, Bammens B. Association of HO-1 (GT)n Promoter Polymorphism and Cardiovascular Disease: a Reanalysis of the Literature. The Canadian journal of cardiology. 2015;32(2):160-168.
Abraham NG, Junge J, Drummond GS. Translational Significance of Heme Oxygenase in Obesity and Metabolic Syndrome. Trends in pharmacological sciences. 2016;37(1):17-36.
Bruls WA, Slaper H, van der Leun JC, Berrens L. Transmission of human epidermis and stratum corneum as a function of thickness in the ultraviolet and visible wavelengths. Photochemistry and photobiology. 1984;40(4):485-494.
Lim HW, Naylor M, Honigsmann H, et al. American Academy of Dermatology Consensus Conference on UVA protection of sunscreens: summary and recommendations. Washington, DC, Feb. 4, 2000. Journal of the American Academy of Dermatology. 2001;44(3):505-508.
Kerr AC, Ferguson J, Attili SK, et al. Ultraviolet A1 phototherapy: a British Photodermatology Groupworkshop report. Clinical and experimental dermatology. 2012;37(3):219-226.
Anderson RR, Parrish JA. The optics of human skin. The Journal of investigative dermatology. 1981;77(1):13-19.
D'Orazio J, Jarrett S, Amaro-Ortiz A, Scott T. UV radiation and the skin. International journal of molecular sciences. 2013;14(6):12222-12248.
Reeve VE, Domanski D. Immunoprotective haem oxygenase induction by ultraviolet A (320-400 nm) radiation in the mouse is inhibited in interferon-gamma null mice. The British journal of dermatology. 2003;148(6):1189-1193.
Reeve VE, Tyrrell RM. Heme oxygenase induction mediates the photoimmunoprotective activity of UVA radiation in the mouse.

(56) References Cited

OTHER PUBLICATIONS

Proceedings of the National Academy of Sciences of the United States of America. 1999;96(16):9317-9321.

Lin HH, Chen YH, Yet SF, Chau LY. After vascular injury, heme oxygenase-1/carbon monoxide enhances re-endothelialization via promoting mobilization of circulating endothelial progenitor cells. Journal of thrombosis and haemostasis: JTH. 2009;7(8):1401-1408.

Bani-Hani MG, Greenstein D, Mann BE, Green CJ, Motterlini R. A carbon monoxide-releasing molecule (CORM-3) attenuates lipopolysaccharide- and interferon-gamma-induced inflammation in microglia. Pharmacological reports: PR. 2006;58 Suppl:132-144.

Motterlini R, Otterbein LE. The therapeutic potential of carbon monoxide. Nature reviews Drug discovery. 2010;9(9):728-743.

Abraham NG, Kappas A. Pharmacological and clinical aspects of heme oxygenase. Pharmacological reviews. 2008;60(1):79-127.

W.L. Morison, UVA-1 Phototherapy of Lupus Erythematosus, Lupus (1994) 3, 139-141, Macmillan Press Ltd, 1994.

* cited by examiner

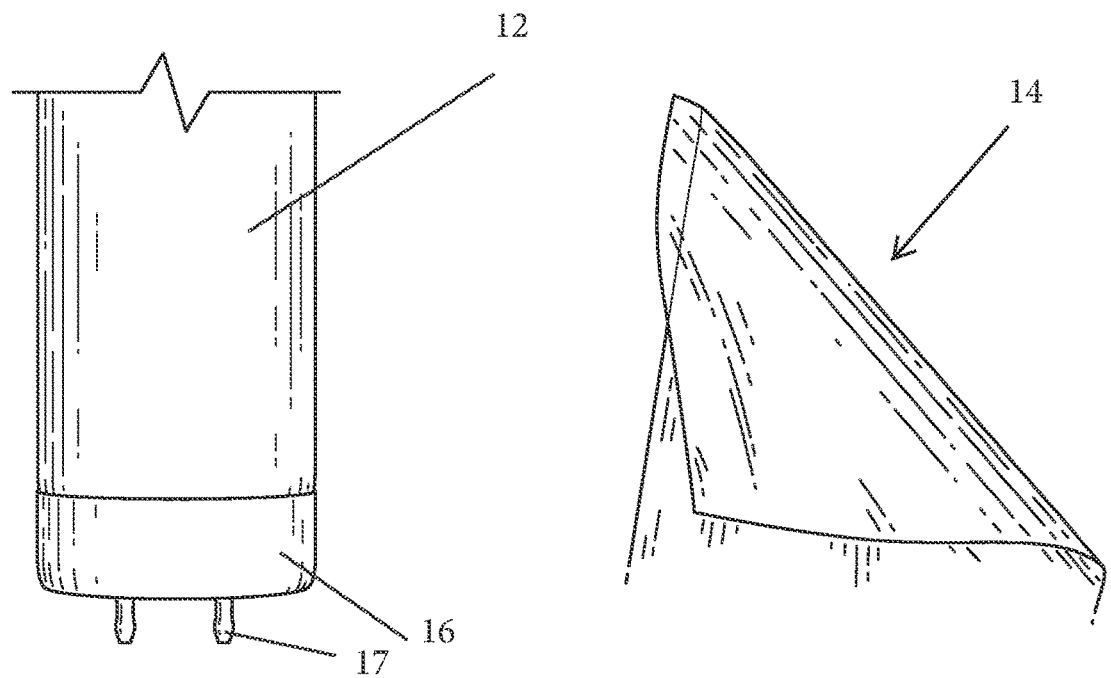
FIG. 8
FIG. 9
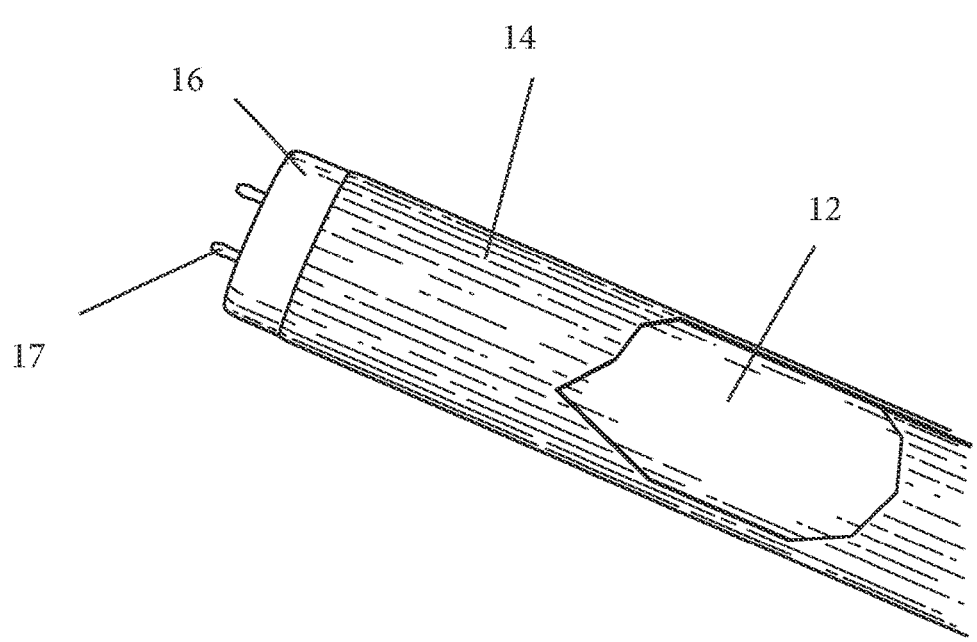
FIG. 10

THERAPY, TREATMENT, AND PROCESS FOR PHOTODYNAMIC INACTIVATION OF COVID-19

CROSS-REFERENCE TO RELATED APPLICATIONS

Priority to and/or the benefit of U.S. Provisional Patent Application Ser. No. 63/014,702 filed on 23 Apr. 2020 and U.S. Provisional Patent Application Ser. No. 63/019,992 filed on 4 May 2020, which are hereby incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a therapy, treatment and process for inactivating and/or killing COVID-19 (Corona Virus Disease 2019), preferably using low-dose, full body, Ultraviolet A1 (UV-A1, 360-400 nm) photon therapy, wherein the UV-A1 photon therapy activates singlet oxygen ($^1O_2$) which directly and indirectly inactivates and/or kills Corona viruses.

2. General Background of the Invention

A current therapy for systemic lupus utilizes low-dose, full body, ultraviolet A1 (UV-A1, 360-400 nm) photon therapy. The UV-A1 photon is unique, as it is the longest of the UV photons and the only one that acts primarily systemically, all the others acting primarily on and in the skin. The UV-A1 photon is also the only known UV-photon that acts primarily by activating $^1O_2$, an intracellular electrophile.

The inactivation of mammalian viruses through photodynamic $^1O_2$-based virus inactivation has been applied with success since the first decades of the last century. The longest wavelengths of ultraviolet (UV) light, ultraviolet-A1 (UV-A1; 340-400 nm), are unique in activating singlet oxygen intracellularly throughout the human system. Low-dose, full body (6 J/cm$^2$) UV-A1, found effective in remitting disease in systemic lupus erythematosus, has also been shown to kill Corona viruses in vitro.

As enveloped viruses, the Corona group is highly susceptible to the inactivation and killing action of $^1O_2$. It has been shown that high levels of $^1O_2$ can be generated in patients lying within a sunbed lined with Philips TL/10R UV-A1 sunlamps (Philips company, Eindhoven, the Netherlands)/covered by Mutzhas UVASUN filters Mutzhas filtes (Mutzhas Company, Munich Germany). This lamp/filter duo allows emission of UV-A1 photons, excluding all others. This maximizes the generation in cells of UV-A1-induced $^1O_2$ and in combination with the cell's own intrinsic production of $^1O_2$, resulting in levels of $^1O_2$ toxic to corona viruses, these levels greater than by any other known means.

A major gene product of $^1O_2$, heme oxygenase-1 (HO-1), is like $^1O_2$ a viricidal acting primarily through its catalytic products, bilirubin and carbon monoxide, adding to the remedial clout of this engine. The UV-A1 photons penetrate to the dermal/epidermal junction capillaries, where they can act on cells circulating through these capillaries and on tissue infiltrating cells, assuring a reach of the $^1O_2$ and HO-1 to all corners of the system.

UV-A1 photons through their activation of singlet oxygen, have the capacity to photo inactivate and kill Corona viruses, including COVID-19 in one or more embodiments of the present invention. It is low-dose, full body (6 J/cm$^2$) UV-A1 irradiation, that has been found effective in remitting disease in systemic lupus erythematosus (SLE), and it is this dose, or slightly more, that has the capacity to kill Corona viruses. Moreover, COVID-19 is an enveloped virus and as such is also uniquely susceptible to UV-A1-$^1O_2$ inactivation and killing.

UV-A1, SLE, Corona Virus, and Photoelectric Effect

In studies in SLE in 1996, low-dose, full body ultraviolet A1 (UV-A1, 340-400 nm) photon irradiation proved effective in remitting symptoms of Systemic Lupus Erythematosus (SLE). UV-A1 photons are the longest in wavelength and lowest in energy of all the solar UV wavelengths photons. By generating $^1O_2$ from a source outside the body, UV-A1 photons supplement naturally generated $^1O_2$, resulting in a level of systemic $^1O_2$ that is potentially greater than through any other means.

$^1O_2$ is the lowest excited state of the diatomic oxygen molecule. It is a gas with physical properties differing only subtly from those of the more prevalent triplet ground state of $O_2$. Accordingly, $^1O_2$ is the common name of an electronically excited state of molecular oxygen. It is less stable than molecular oxygen in the electronic ground state and is typically generated via energy transfer from the excited state of a photosensitizer to the oxygen molecule. In terms of its chemical reactivity, singlet oxygen is highly reactive toward organic compounds. During full body UV-A1 photon irradiation, photosensitizers such as flavins or urocanic acid transfer the photon energy to oxygen, raising baseline or triplet state oxygen to the electronically excited state of molecular oxygen known as $^1O_2$. It has two major remedial actions in SLE: The first is a capacity to promote failed apoptosis and the second, as an electrophile is to activate nuclear factor erythroid 2-related factor 2 (Nrf2), a governor of the activation of the gene for heme oxygenase-1 (HO-1), an enzyme that catalyzes the toxic oxidant heme into carbon monoxide and bilirubin, which act as anti-oxidants.

In 1905, Einstein described the "photo electric effect" wherein photons, interacting with matter, eject electrons. This told us that photons act. The capacity for ultraviolet-A (UV-A, 320-400 nm) photons to ameliorate disease, also implicates a UV photon/chemistry interaction. An early medical study to build upon this UV-A interaction was in 1987. It centered on the New Zealand White/New Zealand Black (B/W) mouse model of systemic lupus erythematosus (SLE). In that model, 3.5 millejoules (mJ) of UV-A irradiation delivered 5x/week, through photons activity, significantly reduced disease activity and eliminated death in the New Zealand Black/New Zealand White (NZB/NZW) mouse. Following up on this, in 1996 low-dose full-body ultraviolet A1 (UV-A1, 340-400 nm) through photon irradiation brought disease reversal in human subjects with SLE. In space and terrestrially, the longest solar wavelengths, those of UV-A1, are proportionately greater in number than all other wavelengths, which are also shorter. The highest proportions of terrestrial UV-A1 wavelengths are in the early morning and late evening (PicoQuant; Life Science; Singlet Oxygen). The most effective way to externally generate cellular singlet oxygen is through this UV-A1 irradiation.

Through the photoelectric effect, a finding that in 1906 won Einstein his first Nobel prize, photons move electrons. The movement becomes visible when UV light is shined on a metal plate. The electrons are ejected from the plate, creating sparks. Building on this observation, UV photons move electrons in nonmetal surfaces, but this is less evident as there is no visible electrical response, or "spark". Nevertheless, the photon's capacity to impact and move electrons should still be sufficient to alter the physical state of matter, with potential to kill or at least injure a virus.

UV-A1 wavelengths having met and interacted in space and terrestrially with the opposing, neutralizing and dilutional effects of the other UV wavelengths, all shorter, make up the final composition of terrestrial UV-A1 wavelengths. This contrasts with the isolated UV-A1 photons emitted from a filtered fluorescent light source used in disease remediation that have been found nowhere else in the solar system. When reaching and penetrating human skin, their effectiveness in generating $^1O_2$, added to internally-derived $^1O_2$, results in a unique overexpression of therapeutic $^1O_2$.

The isolation and exposure to this UV-A1 band of wavelengths, i.e., photons, was accomplished first in 1981 by M. Mutzhas, using phosphor-treated, TL/10R Philips lamps, (Philips International, Eindoven, Netherlands) covered with Mutzhas-pink filters. This combination emitted pure UV-A1, along with some visible, wavelengths. Lacking were the longer, higher energy solar wavelengths of ultraviolet A2 (UV-A2; 320-340 nm) and ultraviolet-B (UV-B; 280-320 nm). These UV-A1 photons brought remediation to patients with SLE.

UV-A1 photon energy is absorbed by photosensitizers within cells and transferred to oxygen, raising this diatomic molecule to its electronically excited state, $^1O_2$. $^1O_2$ is a high energy oxygen having properties that differ from those of the lower energy but more prevalent, triplet ground state oxygen. As a highly reactive oxygen species, $^1O_2$ readily oxidizes a variety of biological molecules, triggering a powerful anti-oxidative response. This anti-oxidative response is at the basis of UV-A1 photon action.

In 1996, low-dose, full body ultraviolet A1 (UV-A1, 340-400 nm) photon irradiation proved effective in remitting signs and symptoms of systemic lupus erythematosus (SLE). By generating $^1O_2$ from a source outside the body, the UV-A1 photons supplement the singlet oxygen normally generated within, resulting in a level of systemic $^1O_2$ never previously realized. Its potential killing power on COVID-19 in one or more embodiments of the present invention is therefore maximized.

During full body UV-A1 photon irradiation, photosensitizers transfer the photon energy to oxygen, engendering $^1O_2$. The human body's intrinsic photosensitizers are not fully known, but in SLE the singlet oxygen has two major remedial actions. The first is a capacity to promote failed apoptosis and the second, to activate heme oxygenase-1 (HO-1), an enzyme that catalyzes the toxic oxidant heme into carbon monoxide and bilirubin antioxidants.

Photons

In space and terrestrially, the longest solar wavelengths, those of UV-A1, predominate over the others. The highest proportions of the terrestrial UV-A1 wavelengths are in the early morning and late evening (PicoQuant; Life Science; Singlet Oxygen).

UV-A1 photons are unique. They are the longest in the UV spectrum, the most effective in generating singlet oxygen and the most effective in penetrating the epidermis to reach the dermal/epidermal junction (DEJ). The DEJ is rich in vascularity, mediating the far-reaching actions of UV-A1 photons. It has three major antiviral actions: first, a UV-A1 photon-induced singlet oxygen mediated photodynamic deactivation (PDI) of enveloped viruses like COVID-19; second, a singlet oxygen-driven activation of Nrf2, governor of the gene activation of heme oxygenase-1 (HO-1), that has the capability of inhibiting or killing viruses; and third, a singlet oxygen damaging of the mitochondrial megapore of the cell incorporating the virus, leading to "immediate apoptosis" of the cell and the virus within. Should apoptosis engage, phagocytosis will follow. This may eliminate most type of viruses and is a mechanism conserved among multi-cellular animals. Mouse cells for example undergo apoptosis in response to influenza virus infection. These apoptotic, virus-infected cells are then targeted for engulfment by macrophages and neutrophils. Induction of apoptosis and the subsequent phagocytosis of virus infected cells appears to be an antiviral innate immune mechanism conserved among multi-cellular organisms.

The HO-1 products CO, biliverdin, bilirubin Fe++ and ferritin, have, additionally, widespread anti-inflammatory and cell protective properties that oppose COVID-19 activated endothelial inflammation and apoptosis and its associated coagulopathy and cytokine storm. It is established that UV-A1 generated singlet oxygen is viricidal toward coronaviruses in vitro, but an in vivo application is needed in the art.

The only UV photon able to generate oxygen and penetrate human cells is that of UV-A1, a photon isolated 40 years ago but never exploited systemically except to alleviate SLE, only now is novelly recognized as a candidate for reaching and killing COVID 19 as discussed herein with regard to the present invention.

The isolation and exposure to this UV-A1 band of wavelengths, i.e., photons, was accomplished in 1981 by M. Mutzhas, using phosphor-treated, TL/10R Philips lamps, (Philips International, Eindoven, Netherlands) covered with Mutzhas-pink filters. This combination emitted pure UV-A1, along with some visible wavelengths. Lacking were the longer, higher energy solar wavelengths of ultraviolet A2 (UV-A2; 320-340 nm) and ultraviolet-B (UV-B; 280-320 nm). This emission brought remediation to patients with SLE.

Full body, low-dose UV-A1 irradiation (6 J/cm$^2$/day) of 26 patients with SLE, 3-5 days a week for three weeks, totaling 18-30 J/cm, significantly reversed signs and symptoms of disease activity. The 6 J/cm$^2$ of irradiation per day is approximately a third of the UV-A1 irradiation a person receives during an hour of Chicago sun in late June, a low dose. For comparison, treatment of the dermatologic disease, morphea, calls for 37 UV-A1 photon irradiation treatments totaling 60-115 J/cm.

Mechanism of Action:

$^1O_2$ triggers the multifunctional regulator nuclear factor erythroid 2-related factor (Nrf2), governor of the gene activation of HO-1. Heme oxygenase-1 (HO-1) is the rate-limiting enzyme of the ferroheme metabolic pathway that is anti-oxidative, anti-inflammatory, anti-apoptotic and anti-smooth muscle hyperplasia. These gene-activated antioxidant responses protect against the standard metabolically-induced oxidative cell damages to maintain homeostasis In normal conditions, Nrf2 is retained in the cytoplasm by its negative regulator Keap-1 which induces its ubiquitination and proteasomal degradation. Under the electrophilic stressor, $^1O_2$, Keap-1 is modified, allowing Nrf2 to move into the nucleus where it activates the transcription of the Nrf2-dependent genes and their proteins, most notably HO-1. $^1O_2$ therefore has two major actions. The first, specific to SLE, is its capacity to open the mitochondrial megapore to activate T-cell apoptosis, flagging in SLE.

However, it is the second action of $^1O_2$, the gene activation of HO-1 that is pertinent, because it can be used to help treat a multitude of disorders. HO-1 is expressed at low levels in most tissues but is highly inducible by a variety of stimuli. It may be among the most critical cytoprotective enzymes, activated during times of cellular stress, which includes inflammation, ischemia, hypoxia, hyperoxia, hyperthermia and radiation (Choi and Alam, 1996). It appears to play a central role in maintaining antioxidant/oxidant homeostasis and in protecting against vascular injury (Abraham and Kappas, 2008).

HO-1 degrades heme groups to biliverdin (BV), carbon monoxide (CO), and free ferrous iron (Fe2+). From the activity of biliverdin reductase, biliverdin is converted to bilirubin which is able to scavenge hydroxyl radicals, singlet oxygen and superoxide anions, as well as prevent protein and lipid peroxidation and exert antioxidant anti-apoptotic and anti-inflammatory activity. The release of free iron by HO-1 prompts the synthesis of the heavy chain of ferritin, which quenches free iron, an oxidant. The activation of the membrane transporter Fe-ATPase permits a cytosolic iron efflux, decreasing the intracellular free Fe2+ content and preventing oxidative cell damage through the Fenton reaction.

CO, the third product of heme catalysis, is best known for its toxicity at high doses. Like cyanide and azide, CO binds to heme in mitochondrial cytochrome c oxidase, altering the mitochondrial respiratory chain, which leads to the chemical asphyxiation of cells. However, the low levels of CO released by HO-1 exhibit more favorable actions.

CO serves as a second messenger, slowing several cellular functions. It accounts for much of the HO-1 induced vasorelaxation, neurotransmission and anti-inflammation. It induces soluble guanylyl cyclase (sGC) and subsequently cyclic guanosine monophosphate (cGMP), through which it mediates its vasodilatory action in vascular smooth cells. It protects against endothelial cell apoptosis by its activation of p38 MAPK. It down-regulates vascular inflammation by modulating macrophage activation, differentiation, and polarization. It acts as a major regulator of vasomotor tone and blood pressure; Singlet oxygen, the progenitor of HO-1 also directly too, and as a progenitor of HO-1 as a potent NF-κB inhibitor, CO prevents TNF-α-induced vascular inflammation. It stimulates blood vessel formation, induces VEGF synthesis in vascular smooth muscle cells and augments the capacity of endothelial cells to respond to exogenous stimuli and to proliferate.

Induction of HO-1 is clearly a neuroprotective response. Amyloid beta (Aβ1)-induced toxic reduction of neuronal proliferation is prevented by Nrf2 overexpression. This protective effect was mimicked by application of the carbon monoxide (CO) releasing molecule CORM-2, supporting observations that HO-1 protection is attributable to its formation of CO. UV-A1 photons by activating Nrf2, bring the other HO-1 products, bilirubin and ferritin, into the opposition toward amyloid beta toxicity in Alzheimer's disease (AD).

Increases of HO-1 can be obtained from the addition of UV-A1 photon therapy but even exposures to early morning or late evening walks resulting in exposures to proportions of terrestrial UV-A1 and to gentle exercise, known to elevate systemic HO-1, adding to HO-1 this inhibitor of cognitive decline are poised to becoming part of future strategies for the treatment of cognitive disorders such as Multiple Sclerosis (MS) and AD. Physical exercise induces hypoxia and has already proven to benefit those with AD. Exercise with its hypoxia and hypoxemia activate the Nrf2/HO-1 signaling pathway while early morning and late evening walks in the park offer maximum natural exposure to UV-A1 and exercise, of benefit to those with cognitive decline.

The UV-A1 photon-generated $^1O_2$, when united with internal chemo-generated $^1O_2$ results in an overexpression of HO-1 in vivo. The capacity of UV-A1 photons to release free heme in vivo results in a further source of heme to be targeted by HO-1, resulting in a potential elevation of HO-1 that is greater than effected in any other circumstance resulting in an overexpression greater than any other known. Reacting against immediate oxidative stresses, this HO-1 presentation is well poised to protect against anticipated oxidant stresses, a major advantage.

This UV-A1 photon-generated HO-1 plays out its defensive role by moving against pulmonary hypertension (PH), interstitial lung disease (ILD), sub-acute lupus erythematosus (SCLE), discoid lupus erythematosus (DLE), anti-phospholipid syndrome (aPS), acute and chronic central nervous system disease and is situated as well to protect against hypertensive cardiovascular disease and metabolic syndrome.

UV-A1 is part of the ultraviolet spectrum. Ultraviolet (UV) radiation is part of the electromagnetic spectrum, encompassing wavelengths between X-rays (0.01 to 10 nm) and visible light (390 to 700 nm), the UV divided into ultraviolet A (UV-A, 320-400 nm) and ultraviolet B (UV-B, 280-320 nm). The UV-A band is further subdivided into ultraviolet-A2 (UV-A2, about 320-340 nm) having properties close to those of UV-B, and ultraviolet-A1 (UV-A1, about 340-400 nm) with properties more closely related to those of visible light.

UV-B wavelengths, damaging to the skin, cause sunburn. They are absorbed by deoxyribonucleic acid (DNA) and therefore penetrate little further than the epidermis. UV-A1 wavelengths are the longest, most abundant, lowest in energy, and deepest penetrating of all the UV wavelengths. They reach photoreceptors in the dermis and sub-dermis, where they infiltrate tissue macrophages, the vasculature, and circulating cells, giving them the widest reach of all the UV photons.

Most important, UV-A1 photons are the only known exogenously delivered activators of singlet oxygen ($^1O_2$), an electronically excited form of molecular oxygen and primary mediator of UV-A1 photon actions. UV-A1 wavelengths were isolated in 1981 with the use of Mutzhas-pink filters (Radiation apparatus: patent number 4,298,005 Nov. 3, 1981). In 1986 using TL/10R Philips lamps (Philips International, Eindoven, The Netherlands), covered by the Mutzhas-pink filters, pure UV-A1 photons were emitted for use in the treatment of patients with SLE. It is this therapeutic action of UV-A1 photons in SLE that has provided a compelling indication for testing the effectiveness of UV-A1 irradiation for remediation of a wide range of other pathologies.

The UV wavelengths make up the portion of the electromagnetic spectrum between X-rays (0.01 to 10 nm) and visible (390 to 700 nm) light. They are conventionally divided into ultraviolet A (UV-A, 320-400 nm), UV-B (280-320 nm) and ultraviolet C (UVC, 200-280 nm). The UV-A band is further subdivided into UV-A2, (320-340 nm) having properties close to those of UV-B and UV-A1 (340-

400 nm) the longest band of UV wavelengths, whose properties are close to those of visible light.

UV-A1 is part of the ultraviolet spectrum. UV photons penetrate the skin in a wavelength dependent manner. During exposure to broad spectrum UV, approximately 100 times more UVA than UVB photons reach the dermis. UV-A1 wavelengths comprise 75% of the UVA band. The isolated UV-A1 wavelengths emitted by the UV-A1 lamps reach deeply, into and beyond the dermis, giving them the widest systemic reach of all the UV wavelengths. They are absorbed as far as the sub dermis, along the way reaching infiltrating macrophages and cells circulating in the dermal and subdermal capillaries. UV-B wavelengths by contrast are absorbed by DNA, epidermal keratinocyte DNA, only 10% reaching the dermis. UV-B is dermal and UV-A1 systemic.

The UV-A1 photon energy absorbed by photosensitizers within cells, is transferred to oxygen, raising this diatomic molecule to its electronically excited state, $^1O_2$. $^1O_2$ has physical properties that distinguish it from the more prevalent triplet ground state oxygen. As a highly reactive Reactive Oxygen Species (ROS), $^1O_2$ readily oxidizes a variety of biological molecules and becomes a primary mediator of UV-A1 photon action.

The electrophile singlet oxygen, activates Nrf2, governor of anti-oxidant forces, to act through HO-1 to reverse cell injury. HO-1 peaks during anticipated injury, such as with the IR that comes with heart surgery or following the administration of hyperoxygenation for pulmonary disease. The supplemental HO-1 generated by UV-A1 exposures can be arranged to reach effectiveness for anticipated injury when the system's own baseline HO-1 does not, as the latter rises only after, not before, injury.

UV-A1 irradiation is dermal, but its photons increase HO-1 expression in the dermis and sub-dermis for as long as three days, providing time for the added HO-1 and its products to act locally and in distant tissues. These actions can be maintained by continued UV-A1 exposures, 2-3 times a week to extend their remedial action. The HO-1 gene can also be transferred by adenovirus vector, a more aggressive, complex and risky technique. Administration of any of the HO-1 products individually, such as CO through CO inhalation or the implantation of a CO-releasing molecule (CO-RM), can increase the effectiveness of the particular effect, as desired. However, these too are risky, invasive, exacting, and expensive techniques. Inhaled CO, for example, sometimes requires hospitalization, cumbersome gas cylinder transport and storage and a need for protection against non-patient exposure. Full-body, low dose, UV-A1 photon irradiation is safe, convenient and physiologic as a means of activating HO-1 systemically, availing patients of the benefits of both catalytically-released CO and the downstream products of HO-1, i.e., BV, Fe, BR, and ferritin.

The following publications are hereby incorporated herein by reference:
1. Costa L, Faustino M A, Neves M G, et al. Photodynamic inactivation of Mammalian viruses and bacteriophages. Viruses. 2012; 4(7):1034-74;
2. McGrath H Jr, Martinez-Osuna P, Lee F A. Ultraviolet-A1 (340-400 nm) irradiation therapy in systemic lupus erythematosus. Lupus; 1996, 5, 269-274;
3. McGrath H Jr, Ultraviolet-A1 irradiation therapy for systemic lupus erythematosus. Lupus. 2017, 26(12); 1239-1251;
4. Ibanez F J, Farias M A, Retamal-Diaz A, et al. Pharmacological induction of heme oxygenase-1 impairs nuclear accumulation of Herpes Simplex virus capsids upon infection. Front Microbiol. 2017; 8:2108;
5. Espinoza J A, Gonzalez P A, Kalergis A M. Am J Pathol. 2017. Modulation of antiviral immunity by heme oxygenase-1. 2017; 187(3): 487-493;
6. Santangelo, R, Mancuso C, Marchetti s, et al. Bilirubin: an endogenous molecule with antiviral activity in vitro. Front Pharmacol. 2012, 3: 36; and
7. Zhang A, Zhao L, Lin N, et al. Carbon monoxide inhibits porcine reproductive and respiratory syndrome virus replication by the cyclic GMP/protein kinase G and NF-kb signaling pathway. J Virol, 2016, 91.

The following publications are also hereby incorporated herein by reference.
1. McGrath H, Jr., Bak E, Michalski J P. Ultraviolet-A light prolongs survival and improves immune function in (New Zealand black×New Zealand white) F1 hybrid mice. Arthritis and rheumatism. 1987; 30(5):557-561.
2. McGrath H, Martinez-Osuna P, Lee F A. Ultraviolet-A1 (340-400 nm) irradiation therapy in systemic lupus erythematosus. Lupus. 1996; 5(4):269-274.
3. Mutzhas M F, Holzle E, Hofmann C, Plewig G. A new apparatus with high radiation energy between 320-460 nm: physical description and dermatological applications. The Journal of investigative dermatology. 1981; 76(1): 42-47.
4. Tuchinda C, Kerr H A, Taylor C R, et al. UVA1 phototherapy for cutaneous diseases: an experience of 92 cases in the United States. Photodermatology, photoimmunology & photomedicine. 2006; 22(5):247-253.
5. Morita A, Werfel T, Stege H, et al. Evidence that singlet oxygen-induced human T helper cell apoptosis is the basic mechanism of ultraviolet-A radiation phototherapy. The Journal of experimental medicine. 1997; 186(10):1763-1768.
6. Tyrrell R M. Solar ultraviolet A radiation: an oxidizing skin carcinogen that activates heme oxygenase-1. Antioxidants & redox signaling. 2004; 6(5):835-840.
7. Stief T W. The physiology and pharmacology of singlet oxygen. Medical hypotheses. 2003; 60(4):567-572.
8. Kanofsky J R. Singlet oxygen production by biological systems. Chemico-biological interactions. 1989; 70(1-2): 1-28.
9. Graindorge D, Martineau S, Machon C, et al. Singlet Oxygen-Mediated Oxidation during UVA Radiation Alters the Dynamic of Genomic DNA Replication. PloS one. 2015; 10(10): e0140645.
10. McGrath H, Jr. Ultraviolet-A1 irradiation therapy for systemic lupus erythematosus. Lupus. 2017; 26(12):1239-1251.
11. Debartolo A. Lupus Underground Evanston, Ill.: Hyde Park Media 2004.
12. Chung S W, Liu X, Macias A A, Baron R M, Perrella M A. Heme oxygenase-1-derived carbon monoxide enhances the host defense response to microbial sepsis in mice. The Journal of clinical investigation. 2008; 118(1): 239-247.
13. Wegiel B, Hedblom A, Li M, et al. Heme oxygenase-1 derived carbon monoxide permits maturation of myeloid cells. Cell death & disease. 2014; 5: e1139.
14. Alonso J R, Cardellach F, Lopez S, Casademont J, Miro O. Carbon monoxide specifically inhibits cytochrome c oxidase of human mitochondrial respiratory chain. Pharmacology & toxicology. 2003; 93(3):142-146.
15. Ryter S W, Alam J, Choi A M. Heme oxygenase-1/carbon monoxide: from basic science to therapeutic applications. Physiological reviews. 2006; 86(2):583-650.

16. Hanafy K A, Oh J, Otterbein L E. Carbon Monoxide and the brain: time to rethink the dogma. Current pharmaceutical design. 2013; 19(15):2771-2775.
17. Kocer G, Nasircilar Ulker S, Senturk U K. The contribution of carbon monoxide to vascular tonus. Microcirculation (New York, N.Y.: 1994). 2018; 25(7): e12495.
18. Silva G, Cunha A, Gregoire I P, Seldon M P, Soares M P. The antiapoptotic effect of heme oxygenase-1 in endothelial cells involves the degradation of p38 alpha MAPK isoform. Journal of immunology (Baltimore, Md.: 1950). 2006; 177(3):1894-1903.
19. Durante W. Protective role of heme oxygenase-1 against inflammation in atherosclerosis. Frontiers in bioscience (Landmark edition). 2011; 16:2372-2388.
20. Sammut I A, Foresti R, Clark J E, et al. Carbon monoxide is a major contributor to the regulation of vascular tone in aortas expressing high levels of haeme oxygenase-1. British journal of pharmacology. 1998; 125 (7):1437-1444.
21. Motterlini R, Gonzales A, Foresti R, Clark J E, Green C J, Winslow R M. Heme oxygenase-1-derived carbon monoxide contributes to the suppression of acute hypertensive responses in vivo. Circulation research. 1998; 83(5):568-577.
22. Choi S, Kim J, Kim J H, et al. Carbon monoxide prevents TNF-alpha-induced eNOS downregulation by inhibiting N F-kappaB-responsive miR-155-5p biogenesis. Experimental & molecular medicine. 2017; 49(11): e403.
23. Loboda A, Jazwa A, Grochot-Przeczek A, et al. Heme oxygenase-1 and the vascular bed: from molecular mechanisms to therapeutic opportunities. Antioxidants & redox signaling. 2008; 10(10):1767-1812.
24. Dulak J, Jozkowicz A, Foresti R, et al. Heme oxygenase activity modulates vascular endothelial growth factor synthesis in vascular smooth muscle cells. Antioxidants & redox signaling. 2002; 4(2):229-240.
25. Hettiarachchi N T, Boyle J P, Dallas M L, Al-Owais M M, Scragg J L, Peers C.
Heme oxygenase-1 derived carbon monoxide suppresses Abeta1-42 toxicity in astrocytes. Cell death & disease. 2017; 8(6): e2884.
26. Kurucz A, Bombicz M, Kiss R, et al. Heme Oxygenase-1 Activity as a Correlate to Exercise-Mediated Amelioration of Cognitive Decline and Neuropathological Alterations in an Aging Rat Model of Dementia. BioMed research international. 2018; 2018:7212861.
27. Cass S P. Alzheimer's Disease and Exercise: A Literature Review. Current sports medicine reports. 2017; 16(1):19-22.
28. Wang Y, Chai Y, He X, et al. Intermittent hypoxia simulating obstructive sleep apnea causes pulmonary inflammation and activates the Nrf2/HO-1 pathway. Experimental and therapeutic medicine. 2017; 14(4): 3463-3470.
29. Potue P, Wunpathe C, Maneesai P, Kukongviriyapan U, Prachaney P, Pakdeechote P. Nobiletin alleviates vascular alterations through modulation of Nrf-2/HO-1 and MMP pathways in 1-NAME induced hypertensive rats. Food & function. 2019.
30. Daenen K E, Martens P, Bammens B. Association of HO-1 (GT)n Promoter Polymorphism and Cardiovascular Disease: A Reanalysis of the Literature. The Canadian journal of cardiology. 2016; 32(2):160-168.
31. Abraham N G, Junge J M, Drummond G S. Translational Significance of Heme Oxygenase in Obesity and Metabolic Syndrome. Trends in pharmacological sciences. 2016; 37(1):17-36.
32. Bruls W A, Slaper H, van der Leun J C, Berrens L. Transmission of human epidermis and stratum corneum as a function of thickness in the ultraviolet and visible wavelengths. Photochemistry and photobiology. 1984; 40(4):485-494.
33. Lim H W, Naylor M, Honigsmann H, et al. American Academy of Dermatology Consensus Conference on UVA protection of sunscreens: summary and recommendations. Washington, D C, Feb. 4, 2000. Journal of the American Academy of Dermatology. 2001; 44(3):505-508.
34. Kerr A C, Ferguson J, Attili S K, et al. Ultraviolet A1 phototherapy: a British Photodermatology Group workshop report. Clinical and experimental dermatology. 2012; 37(3):219-226.
35. Anderson R R, Parrish J A. The optics of human skin. The Journal of investigative dermatology. 1981; 77(1): 13-19.
36. D'Orazio J, Jarrett S, Amaro-Ortiz A, Scott T. UV radiation and the skin. International journal of molecular sciences. 2013; 14(6):12222-12248.
37. Reeve V E, Domanski D. Immunoprotective haem oxygenase induction by ultraviolet A (320-400 nm) radiation in the mouse is inhibited in interferon-gamma null mice. The British journal of dermatology. 2003; 148(6): 1189-1193.
38. Reeve V E, Tyrrell R M. Heme oxygenase induction mediates the photoimmunoprotective activity of UVA radiation in the mouse. Proceedings of the National Academy of Sciences of the United States of America. 1999; 96(16):9317-9321.
39. Lin H H, Chen Y H, Yet S F, Chau L Y. After vascular injury, heme oxygenase-1/carbon monoxide enhances re-endothelialization via promoting mobilization of circulating endothelial progenitor cells. Journal of thrombosis and haemostasis: JTH. 2009; 7(8):1401-1408.
40. Bani-Hani M G, Greenstein D, Mann B E, Green C J, Motterlini R. A carbon monoxide-releasing molecule (CORM-3) attenuates lipopolysaccharide- and interferon-gamma-induced inflammation in microglia. Pharmacological reports: P R. 2006; 58 Suppl:132-144.
41. Motterlini R, Otterbein L E. The therapeutic potential of carbon monoxide. Nature reviews Drug discovery. 2010; 9(9):728-743.
42. Abraham N G, Kappas A. Pharmacological and clinical aspects of heme oxygenase. Pharmacological reviews. 2008; 60(1):79-127.

The following publications are also hereby incorporated herein by reference thereto.

1. W. L. MORISON, UVA-1 Phototherapy of Lupus Erythematosus, Lupus (1994) 3, 139-141, Macmillan Press Ltd, 1994;
2. M. C. A. Polderman, S. le Cessie, T. W. J. Huizinga. S. Pavel, Efficacy of UVA-1 cold light as an adjuvant therapy for systemic lupus erythematosus, Rheumatology 2004; 43:1402-1404, Advance Access publication 10 Aug. 2004;
3. H McGrath Jr., Elimination of anticardiolipin antibodies and cessation of cognitive decline in a U V-A1-irradiated systemic lupus erythematosus patient, Lupus (2005) 14, 859-861;
4. H McGrath Jr., Elimination of anticardiolipin antibodies and cessation of cognitive decline in a U V-A1-irradiated systemic lupus erythematosus patient, Lupus (2005) 14 1-3;
5. Benjamin Jabara, M D: Mollie Dahlgren, M D: and Hugh McGrath, Jr., M D, Interstitial Lung Disease and Pulmonary Hypertension Responsive to Low Dose UVA1 Irradiation in Lupus, PMC 2011 Jun. 1;
6. Benjamin Jabara, M D: Mollie Dahlgren, M D, and Hugh McGrath, Jr., M D. Interstitial Lung Disease and Pulmonary Hypertension Responsive to Low-Dose UVA1 Irradiation in Lupus, PMC 2010 Jun. 2;
7. S. Pavel, Light therapy (with UV A-1) for SLE patients: is it a good or bad idea?, Rheumatology (June 2006) 45 (6): 653-655 (First published online: Mar. 7, 2006);
8. JOSE F. MOLINA and HUGH McGRATH Jr., Longterm Ultraviolet-A1 Irradiation Therapy in Systemic Lupus Erythematosus, The Journal of Rheumatology 1997; 24:6, 1072-1074;
9. HUGH McGRATH Jr., Prospects for UV-A1 therapy as a treatment modality in cutaneous and systemic L E, Lupus (1997) 6, 209-2: 7;
10. Y Menon, K McCarthy and H McGrath Jr., Reversal of brain dysfunction with U V-A1 irradiation in a patient with systemic lupus, Lupus (2003) 12, 479-482;
11. M C A Polderman, C van Kooten, N P M Smit, S W A Kamerling, Ultraviolet-A (UVA-1) radiation suppresses immunoglobuli activated B lymphocytes in vitro, Clin Exp Immunol. 2006 Sep. 1; 145(3): 528-534;
12. H McGrath, Jr., Ultraviolet-A 1 irradiation therapy for systemic lupus erythematosus, LUPUS, 2017 October; 26(12): 1239-1251 (Published online 2017 May 8);
13. A. Szegedi, E. Simics, M. Aleksza, I. Horkay, K. Gaal, S. Sipka, J. Hunyadi and E. Kiss, UltravioletrA1 phototherapy modulates Th1/Th2 and Tc1/Tc2 balance in patients with systemic/lupus erythematosus, Rheumatology 2005, 44:925-931, Advance Access publication, 12 Apr. 2005; and
14. Hugh McGrath, Jr., Ultraviolet A V (340-400 nm) Irradiation and Systemic Lupus Erythematosus, 1087-0024/99, Copyright© 1999, by The Society for Investigative Dermatology, Inc., VOL. 4, NO 1 Sep. 1999; and
15. McGrath H, Martinez-Osuna P, Lee F A. Ultraviolet-A1 (340-400 nm) irradiation therapy in systemic lupus erythematosus. Lupus. 1996; 5(4):269-274.

The following publications are also hereby incorporated herein by reference.
1. Costa L, Faustino M A, Neves M G, et al. Photodynamic inactivation of Mammalian viruses and bacteriophages. Viruses. 2012; 4(7):1034-74.
2. McGrath H Jr, Martinez-Osuna P, Lee F A. Ultraviolet-A1 (340-400 nm) irradiation therapy in systemic lupus erythematosus. Lupus; 1996, 5, 269-274.
3. McGrath H Jr, Ultraviolet-A1 irradiation therapy for systemic lupus erythematosus. Lupus. 2017, 26(12); 1239-1251.
4. Ibanez F J, Farias M A, Retamal-Diaz A, et al. Pharmacological induction of heme oxygenase-1 impairs nuclear accumulation of Herpes Simplex virus capsids upon infection. Front Microbiol. 2017; 8:2108.
5. Espinoza J A, Gonzalez P A, Kalergis A M. Am J Pathol. 2017. Modulation of antiviral immunity by heme oxygenase-1. 2017; 187(3): 487-493,
6. Santangelo, R, Mancuso C, Marchetti s, et al. Bilirubin: an endogenous molecule with antiviral activity in vitro. Front Pharmacol. 2012, 3: 36.
7. Zhang A, Zhao L, Lin N, et al. Carbon monoxide inhibits porcine reproductive and respiratory syndrome virus replication by the cyclic GMP/protein kinase G and N F-kb signaling pathway. J Virol, 2016, 91.

The following U.S. Patents and Patent Publications are incorporated herein by reference:

| PAT. NO. | TITLE | ISSUE DATE |
| --- | --- | --- |
| 4,151,030 | METHOD FOR JOINTING OF DIELECTRIC OPTICAL WAVEGUIDES | Apr. 24, 1979 |
| 4,298,005 | RADIATION APPARATUS | Nov. 3, 1981 |
| 4,683,379 | LAMP FOR EMISSION OF RADIATION IN UV AND VISIBLE LIGHT RANGES OF THE SPECTRUM | Jul. 28, 1987 |
| 5,658,722 | PROCESS FOR THE STERILIZATION OF BIOLOGICAL COMPOSITIONS USING UVA1 IRRADIATION | Aug. 19, 1997 |
| 6,063,108 | METHOD AND APPARATUS FOR LOCALIZED LOW ENERGY PHOTON THERAPY (LEPT) | May 16, 2000 |
| 6,537,304 | ISCHEMIA LASER TREATMENT | Mar. 25, 2003 |
| 6,635,642 | PARP INHIBITORS, PHARMACEUTICAL COMPOSITIONS COMPRISING SAME, AND METHODS OF USING SAME | Oct. 21, 2003 |
| 6,902,563 | IRRADIATION DEVICE FOR THERAPEUTIC TREATMENT OF SKIN AND OTHER AILMENTS | Jun. 7, 2005 |
| 7,041,343 | METHOD FOR PROVIDING A SUBSTRATE STRUCTURE FOR ORIENTED NEURITE OUTGROWTH, SUBSTRATE STRUCTURE, AND DEVICE FOR MONITORING NEURON | May 9, 2006 |
| 10,517,538 | SYSTEMS, DEVICES AND METHODS FOR SENSING PHYSIOLOGIC DATA AND DRAINING AND ANALYZING BODILY FLUIDS | Dec. 31, 2019 |
| 2002/0155098 | METHODS FOR TREATING THE INFLAMMATORY COMPONENT OF A BRAIN DISORDER | Oct. 24, 2002 |
| 2003/0202939 | METHODS FOR USING ANNEXIN FOR DETECTING CELL DEATH IN VIVO AND TREATING ASSOCIATED CONDITIONS | Oct. 30, 2003 |
| 2004/0087485 | EDUCATED NKT CELLS AND THEIR USES IN THE TREATMENT OF IMMUNE-RELATED DISORDERS | May 6, 2004 |
| 2005/0197681 | METHOD AND DEVICE FOR THE TREATMENT OF MAMMALIAN TISSUES | Sep. 8, 2005 |
| 2006/0184214 | LOW INTENSITY LIGHT THERAPY FOR TREATMENT OF RETINAL, MACULAR, AND VISUAL PATHWAY DISORDERS | Aug. 17, 2006 |
| 2007/0179570 | WEARABLE DEVICE AND METHOD FOR | Aug. 2, 2007 |

| PAT. NO. | TITLE | ISSUE DATE |
|---|---|---|
| 2010/0121420 | PROVIDING PHOTOTHERAPY TO THE BRAIN UVA1-LED PHOTOTHERAPY DEVICE AND METHOD | May 13, 2010 |

There is a need for a phototherapy, treatment and process that is safe and effective in treating persons suffering from a Corona virus, including COVID-19.

There is no known method that has targeted treatment of a patient having a Corona virus, including COVID-19; known studies and applications have all been in vitro.

BRIEF SUMMARY OF THE INVENTION

Ultraviolet-A1 (UV-A1 ~340 to 400 nm) irradiation, developed approximately 40 years ago and 25 years ago found effective in the treatment of systemic lupus erythematosus (SLE), is novelly used in the present invention as an effector in the protection against and elimination of COVID-19 disease. Unlike vaccination, UV-A1 as a physically damaging agent toward COVID-19 has little possibility of triggering mutational resistance. Low-dose, full body UV-A1 irradiation eliminates corona viruses through photodynamic deactivation (PDI), preprogrammed cell apoptosis and activation of heme oxygenase-1 (HO-1). PDI has been available since the first decades of the last century but is effective only in vitro. An advance to in vivo has now become possible because of the use of UV-A1 irradiation. UV-A1 photons penetrate to the dermal/epidermal junction vasculature to act, in effect, systemically.

After contacting endogenous photosensitizers, UV-A1 photons transfer their energy to oxygen, engendering singlet oxygen, the mediator of PDI. Singlet oxygen inhibits viruses not only through PDI but by engendering apoptosis of the cells containing the virus and by the singlet oxygen-mediated generation of heme oxygenates-1 (HO-1). In addition to eliminating corona viruses, the HO-1 products, carbon monoxide (CO), biliverdin (BV), iron (Fe++) and bilirubin (BR) have proven effective in combating inflammation and cytokine storm, characteristics of COVID-19. The UV-A1 photon irradiation, in addition, eliminates anti-cardiolipin antibodies (aCL) and brain fog, stand-out expressions of COVID-19 and UV-A1 fosters anti-coagulation, in opposition to the pro-coagulation state triggered by COVID-19.

A therapy developed by the same inventor of the present invention activates singlet oxygen ($^1O_2$) to reverse systemic lupus erythematosus. The therapy rests on the capacity of UV-A1 irradiation to produce singlet oxygen. The preferred treatment apparatus to do this includes a Mutzhas UV-A1 filter fitted atop a Philips UV-A1 lamp, the two emitting UV-A1 photons purer than they can be found anywhere in the solar system. UV-A1 photons can penetrate the skin deeply enough to reach the vasculature (with its circulating blood), giving the UV-A1 photons a systemic therapeutic effect.

Eliminating the other UV wavelengths, UVC, UVB and UV-A2, with the lamp/filter, eliminates the inhibitory and dilutional effects of these shorter wavelengths toward UV-A1. The UV-A1 photons delivered to patients through the lamp/filter engine are in a pure state, more so than can be found anywhere, either terrestrially or throughout the solar system. This results in the generation of enough singlet oxygen to reverse systemic lupus erythematosus disease activity and, in the present invention, to kill Corona viruses in vivo.

Aside from the direct toxic effect of singlet oxygen on intracellular COVID-19, the electrophile singlet oxygen activates Nrf2, a master transcriptional activator of protective genes that activates the gene for heme-oxygenase, the major mediator of homeostasis in the body. Heme oxygenase is a catalytic enzyme that breaks down hemoglobin into carbon monoxide (CO) and biliverdin (BV), isomerized immediately to bilirubin (BR), all three of which are antioxidants adding to the direct antagonistic effect of singlet oxygen on COVID-19.

Embodiments of the therapy, treatment and process of the present invention solves the problems confronted in the art in a simple and straightforward manner. In one or more preferred embodiments, the therapy and treatment process of the present invention includes novel use of an irradiator for full body irradiation of a patient with a corona virus and/or COVID-19 (e.g., an irradiator can be a sunbed or standing chamber that is lined with lamps or light bulbs, preferably covered by filters, that are adapted to emit UV-A1 and possibly also visible light photons, while preferably excluding at least substantially all other UV photons or other potentially harmful UV photons). With total body irradiation, preferably with eyes covered, the UV-A1 photons can penetrate the body of a patient, reaching the sub-dermal circulating blood to activate singlet oxygen within the cells of the flowing blood. The singlet oxygen can inactivate, kill and/or denature the Corona viruses, including COVID-19. The exposure of dermal and subdermal blood to UV-A1 photons increases the patient's body's cellular level of singlet oxygen maximally. Furthermore, heme oxygenase-1, a major gene product of $^1O_2$, is itself viricidal, due primarily to its catalytic products, carbon monoxide and bilirubin that are both anti-viral. This adds further to the remedial clout of this engine.

Use of UV-A1 irradiation in one or more preferred embodiments of the present invention is an approach to killing COVID-19 with little possibility of triggering mutational resistance. Low-dose, full body UV-A1 irradiation eliminates corona viruses through photodynamic deactivation (PDI). PDI has been available since the first decades of the last century but is effective only in vitro. An advance to in vivo has now become possible because of the use of UV-A1 irradiation. UV-A1 photons penetrate to the dermal/epidermal junctional vasculature to act systemically when contacting endogenous photosensitizers, UV-A1 photons can transfer their energy to oxygen, engendering singlet oxygen, an agent of PDI. Singlet oxygen inhibits viruses not only through PDI but via the singlet oxygen mediated generation of heme oxygenates-1 (HO-1). In addition to eliminating Corona viruses, the HO-1 products, carbon monoxide (CO), Biliverdin (BV), iron (Fe++) and the bilirubin (BR) have proven effective in combating inflammation and cytokine storm. The UV-A1 photon irradiation also eliminates anti-cardiolipin antibodies (aCL) and brain fog, while fostering anti-coagulation. The full-body UV-A1 irradiation effectiveness in SLE underscores its systemic action.

Under one or more preferred embodiments of the present invention, several (e.g., about 2 to 3 days per week, about 20 to 30 minute exposures, for about 2 to 3 months or longer as may be needed to UV-A1 full body irradiation at 6 to 8 J/cm$^2$) exposures to UV-A1 light can be used to treat or combat brain fog. In other preferred embodiments, several (e.g., about 2 to 3 days per week, about 20 to 30 minute exposures for about 2 to 3 months or longer as may be needed to UV-A1 full body irradiation at 7 to 15 J/cm$^2$) exposures to UV-A1 light can also be used to treat or combat brain fog. In other preferred embodiments, several (e.g., about 2 to 3 days per week, about 20 to 30 minute exposures for about 2 to 4 weeks or longer as may be needed to UV-A1 full body irradiation at 6 to 15 J/cm$^2$) exposures to UV-A1 light can also be used to treat or combat brain fog. Some symptoms, e.g., brain fog can take longer to subside, e.g., several weeks to a couple months.

Although the Corona virus (COVID-19) pandemic is coming under the control of vaccination, it is an RNA virus, highly susceptible to mutation. Mutants have already been reported. UV-A1 irradiation of the present invention, a nonphysiologically exploited physical force uses photons that are the longest in the ultraviolet spectrum, capable of generating singlet oxygen and capable of penetrating the epidermis of a person to reach the vasculature at the dermal/epidermal junction, giving the photons what is essentially systemic access to the body.

UV-A1-generated singlet oxygen is antiviral and fibrinolytic (open blood flow). It is an electronically excited form of molecular oxygen that kills viruses, especially enveloped viruses such as COVID-19. In addition, it defends against COVID-19-induced inflammation by next generation of HO-1.

In one or more preferred embodiments of the treatment process and therapy of the present invention, a patient's full body is exposed to UV-A1 irradiation, preferably sparing only the eyes, which can be covered with sunglasses, and personal parts of the body lightly clad with undergarments.

Preferably at least enough of a patient's body is exposed to activate a total body increase in $^1O_2$. The UV-A1 light works on the blood flowing in the vessels under it, which is eventually all the blood within a person's body, taking minutes longer if fewer vessels are exposed at any one time. Full body exposure is thus preferred as less time is required under the UV-A1 light, but desired results may still be obtained over longer periods of time if less than the patient's full body is exposed.

As mentioned, dermatologists have used UV-A1 light for its impact on a patient's skin alone and not for its systemic effect. Using UV-A1 light for its systemic action, which, of all UV, is predominately due to the UV-A1 wavelengths, because of their ability to penetrate to the sub-dermal capillary network, is a novel and important feature of the present invention directed to targeting the Corona virus including COVID-19. The UV-A1 photons activate singlet oxygen, $^1O_2$, which is an oxyphile capable of activating singlet oxygen to kill viruses intracellularly.

In one or more preferred embodiments, a full body, low-dose UV-A1 irradiation of wavelength between 360 to 400 nm at 8-10 J/cm$^2$/day is administered to a patient with COVID-19 for 20 to 30 minutes for 3 to 4 days per week for 3 to 4 weeks, or longer as may be needed.

In one or more preferred embodiments, a full body, low-dose UV-A1 irradiation of wavelength between 360 to 400 nm at 8-10 J/cm$^2$/day is administered to a patient with COVID-19 for 8 to 30 minutes for 3 to 4 days per week for 3 to 4 weeks, or longer as may be needed.

In one or more preferred embodiments, a full body, low-dose UV-A1 irradiation of wavelength between 340 to 400 nm at 8-10 J/cm$^2$/day is administered to a patient with COVID-19 for 8 to 30 minutes for 2 to 4 days per week for 3 to 4 weeks, or longer as may be needed.

In one or more preferred embodiments, a full body, low-dose UV-A1 irradiation of wavelength between 360 to 400 nm at 6-10 J/cm$^2$/day is administered to a patient with COVID-19 for 20 to 30 minutes for 3 to 4 days per week for 3 to 4 weeks, or longer as may be needed.

In other preferred embodiments, full body, low-dose UV-A1 irradiation of wavelength 340-400 nm at 6-8 J/cm$^2$/day is administered to a patient with COVID-19 for 20 to 30 minutes, 2-3 times a week for 2-4 weeks, or longer as may be needed.

In other preferred embodiments, a full body, low-dose of UV-A1 irradiation of wavelength 340-400 nm (8-15 J/cm$^2$/day) is administered to a patient with COVID-19 for 6 to 8 minutes 2-3 days per week for 2-4 weeks, or longer as may be needed.

In other preferred embodiments, full body, low-dose UV-A1 irradiation of wavelength 340-400 nm at 6-15 J/cm$^2$/day is administered to a patient with COVID-19 for 6 to 30 minutes, 2-4 times a week for 2-4 weeks, or longer as may be needed.

An example of an irradiator that can be utilized in one or more preferred embodiments of the present invention is a sunbed of the bench and canopy type, e.g., a ALISUN Company 1000 combi sunbed of the bench and canopy type, that is lined with Philips TL/10R UV-A1 sunlamps (Philips company, Eindhoven, the Netherlands) covered by Mutzhas UVASUN filters Mutzhas filters (Mutzhas Company, Munich Germany). This lamp/filter duo allows emission of UV-A1 photons, while excluding all other UV photons, or at least substantially all other UV photons. Visible light is not excluded in this irradiator and appears blue. This maximizes the generation in cells of UV-A1-induced singlet oxygen and in combination with the cell's own intrinsic production of singlet oxygen, delivers $^1O_2$ at levels greater than any other known means.

In other embodiments, an irradiator can be of the type adapted to expose a patient to UV-A1 light while standing, and preferably illuminated by Phillips™ UV-A1 lamps and screened by Mutzhas™ UV-A1 filters. Using a standing chamber can potentially have greater treatment benefits because UV-A1 effect is oxygen dependent. The side with the most pressure, i.e., the down side when a person lies down, is under more pressure in a canopy/bench arrangement giving it less blood flow and therefore less oxygen. In using the bench canopy for tanning, for example, manufacturer's have reported less tanning effect on this underside. Use of a standing irradiator can prevent pressure being applied to a side of a person's body.

UV-A1 photons can kill the Corona viruses because unlike all other UV wavelengths, UV-A1 light (photons) reach all the blood's cells flowing through the small blood vessels in the sub-dermis, which is heavily vascular, whereas the shorter wavelengths of UV-A2 and UV-B reach little further than the epidermis, i.e., the outer skin.

UV-A1 photons are safer than other ultraviolet photons and low doses are unlikely to have negative side effects or impacts on the patients. People receive high levels of UV-A1 in sunlight, about 75% of the total UV. Because the atmosphere blocks the shorter wavelengths more than UV-A1, people get proportionally more UV-A1 in the early morning or in the evening when the sun has more atmosphere to block the shorter wavelengths and therefore proportionately less UV-A2 and UV-B. Ultraviolet C (280-232 nm) terrestrial levels are zero because it is completely blocked by the atmosphere. A patient exposed to a dose of 360 to 400 nm at (8-10 J/cm²/day) is receiving what is far below the sunburn level and will experience no more than a light tan, and that likely only if they are Caucasian. UV-A1 is the least toxic of the UV wavelengths and it would take very little time to determine if a patient with mild disease gets better or worse.

Mutzhas Isolated UV-A1

As discussed, M. Mutzhas isolated the UV-A1 wavelength band in 1981 using his "Mutzhas-pink" filters. In 1986, applying full body, low dose (6-10 J/cm²) UV-A photon irradiation, UV-A incorporating UV-A1, McGrath et al. reversed disease activity in mice with lupus. This indicated for the first time that UV-A photon irradiation can work in vivo. In 1996, using the above-described Mutzhas-pink filters to cover Philips TL/10R Philips UV-A1 lamps (Philips International, Eindoven, the Netherlands), pure UV-A1 photons reversed SLE disease activity in humans with the disease.

The low-dose full body UV-A1 photons emitted by the Philips UV-A1 lamps and screened by Mutzhas-pink filters are of a purity unknown to exist elsewhere. It is these photons that penetrate the epidermis to reach the Dermal/Epidermal junction, and interface with the body that escapes the competing, inhibitory, and dilutional effects of all other UV photons.

ACE Receptor

The COVID-19 virus uses the human angiotensin-converting enzyme 2 (ACE 2) receptor to enter the body. This receptor is body-wide and binds to the COVID-19 virus spike, offering the COVID-19 virus broad access to the vascular endothelium and therefore to nearly all human organs. The receptor can be found on the surface of type II alveolar epithelial cells in the lungs, but also on the endothelium of the vasculature surrounding the alveoli, making the lungs a prime target for COVID-19, slated to sustain a double-dose of pulmonary virus entry.

Endothelium

Under one or more embodiments of the present invention, UV-A1 photons reach the dermal ACE-2 receptor-studded endothelium throughout the body, the UV-A1-generated singlet oxygen and its downstream HO-1 products offer alleviation of COVID-19-generated endothelial inflammation and its resulting impairment of microcirculatory function and enhanced coagulopathy. This can be directed to slow the COVID-19-derived life-threatening complications of venous thromboembolic disease and multiple organ involvement. The powerful antioxidant HO-1 slows down cytokine storm and death, two notables in COVID-19 infection.

Endothelial cell dysfunction with its resulting impaired microcirculatory function contributes to life-threatening complications of COVID-19, such as venous thromboembolic disease and multiple organ involvement. Increased CO levels, the result of UV-A1 activation of singlet oxygen/HO-1 temper the viral-induced injury and death of endothelial cells.

ARDS

Accordingly, COVID-19 infection proceeds apace in the lungs. Acute respiratory distress syndrome (ARDS), a lung injury that allows fluid to leak into the lungs, occurs 3-9 days after the onset of COVID-19 infection and accounts for 70% of the ensuing deaths. Ventilator support is usually needed.

Artificial Ventilation

The downside of mechanical ventilation is that it can touch off inflammation through a cytokine response, induced by the high tidal volume of respiration, which decreases levels of the anti-inflammatory CO. Under one or more preferred embodiments of the present invention, the decreases in CO in COVID-19 patients can be minimized by reducing pulmonary overdistention or by restoring CO through the induction of full body UV-A1, generator of HO-1. This also represses ventilator-associated inflammation by removing the pro-inflammatory molecule heme and releasing the anti-inflammatory bile pigments, biliverdin and bilirubin. HO-1/CO may protect against inflammation and cytokine storm even further by decreasing IL-6, a pivotal generator of inflammation; by increasing IL-10, a major anti-inflammatory cytokine; and by driving macrophage polarization from the pro-inflammatory M1 macrophage to the anti-inflammatory M2 macrophage, the shift ushering in macrophage opposition to the development of inflammation and cytokine storm.

Under one or more preferred embodiments of the present invention, several (e.g., about 2 to 3 days per week, about 20 to 30 minute exposures, for about 2 to 4 weeks or longer as needed to UV-A1 full body irradiation at 6 to 15 J/cm²) exposures to UV-A1 light can help minimize the decreases in CO in COVID-19 patients by reducing pulmonary overdistention or by restoring CO through the induction of full body UV-A1. Under one or more preferred embodiments of the present invention, several (e.g., about 2 to 3 days per week, about 20 to 30 minute exposures, for about 2 to 3 months or longer as needed to UV-A1 full body irradiation at 6 to 8 J/cm²) exposures to UV-A1 light can help minimize the decreases in CO in COVID-19 patients by reducing pulmonary overdistention or by restoring CO through the induction of full body UV-A1. In other preferred embodiments, several (e.g., about 2 to 3 days per week, about 20 to 30 minute exposures, for about 2 to 3 months or longer as may be needed to UV-A1 full body irradiation at 7 to 15 J/cm²) exposures to UV-A1 light can help minimize the decreases in CO in COVID-19 patients by reducing pulmonary overdistention or by restoring CO through the induction of full body UV-A1.

Photosensitizers and PDI

In the presence of intrinsic, or following the addition of endogenous photosensitizers (PS), such as flavins, porphyrins and urocanic acid, UV-A1-generated singlet oxygen can trigger photodeactivation (PDI) in vitro. In one or more embodiments of the present invention, PDI is an antiviral strategy directly inactivating viruses in vivo, wherein Mutzhas-filtered UV-A1 lamp-emitted photons can be used for the elicitation of PDI in vivo, the existence of which would be an important step toward control of both COVID-19 and its mutations. The HO-1 release of the heme breakdown products, CO, biliverdin, bilirubin and ferritin, would add capability of inhibiting the virus and diminishing any lingering effects of a prior infection.

It is noted that as discussed herein, UV-A1 wavelengths including the longest but relatively unstudied wavelengths that make up the greater part of the UV-A band can be used in one or more preferred embodiments of the treatment process and therapy of the present invention.

Sunbed Exposures

The lamp/filter UV-A1 design as developed for its remedial action in SLE treatment can be used in one or more preferred embodiments of the present invention. Patients can lie for equal amounts of time prone and supine in a sunbed lined with a lamp/filter, e.g., a Philips TL/10R UV-A1 lamp (Philips company, Eindhoven, the Netherlands), screened with a filter, e.g., a Mutzhas UVASUN filters (Mutzhas Company, Munich Germany) or a Polycast™ filter adapted to filter UV light other than UV-A1 light. When using a Philips TL/10R UV-A1 lamp screened with Mutzhas UVA-SUN filters, virtually 100 percent of the emitted photons are UV-A1, and their intended product, singlet oxygen, is maximized. With these sunbed emissions of singlet oxygen, when added to the cell's intrinsically produced singlet oxygen, (the singlet oxygen from ambient solar UV-A1, and the singlet oxygen from body-wide UV-A1-induced hemolysis), the total levels of singlet oxygen accrued are greater than can be obtained by any other known means. The potentially minor inconvenience and expense of engaging a UV-A1 sunbed is offset by the comfort, safety and high impact of UV-A1 irradiance as an anti-Covid-19 ordnance.

HO-1

Under one or more preferred embodiments of the present invention, after PDI, the second means of protecting against COVID-19 lies in the action of HO-1. UV-A1 irradiation, through its generation of singlet oxygen, activates Nrf2, an in vivo transcription factor for the HO-1 gene. HO-1 catalyzes heme, releasing carbon monoxide (CO), biliverdin, (BV), and ferritin (Fe++), the BV converted to bilirubin (BR) by BV reductase. HO-1 is a kind of stress enzyme, potently antioxidant and regarded as a sensitive and reliable indicator of cellular oxidative stress. The four products, CO, BV, BR and Fe++ are antioxidant and led by CO, down-regulate the inflammatory reaction toward COVID-19 that can progress to an often-lethal cytokine storm. They add to the body's defense against COVID-19, protect endothelial cells, pushing against widespread endothelial inflammation and against its prothrombotic milieu in COVID-19, the CO derepressing the fibrinolytic axis.

The HO-1 system overall is antioxidant. The HO-1 product CO maintains vascular tone, increases angiogenesis, is potently antioxidant and is an intrinsic signaling molecule on a par with nitric oxide. Studies have been based mostly on CO inhalation and metal-based CO-releasing molecules. Far simpler would be use of the more readily available UV-A1-generated-HO-1-engendered CO for testing and treatment.

CO

HO-1 released CO is multifunctional. In cells and animals CO can suppress inflammation, protect tissues from oxidative stress and prevent cell death. It is a gas that helps to restore blood flow to organs threatened by a compromised blood supply via the dilatation of blood vessels and the enhancement of the body's clot-dissolving mechanisms.

Both of the CO products CO and BV are known to act together against viruses, one example being the suppression of bovine viral diarrhea through the repression of virus replication.

Cytokine Storm

A subgroup of patients with severe COVID-19 progress to cytokine storm syndrome. Cytokine storm seems to be an inordinate response to a virus, not seen with standard coronavirus infections. It is characterized by constitutional symptoms systemic inflammation and multiorgan dysfunction that can lead to multiorgan failure if inadequately treated. It is an umbrella term encompassing several disorders of immune dysregulation characterized by constitutional symptoms, systemic inflammation, and multiorgan dysfunction. It is due to elevated levels of circulating cytokines as the immune response to the pathogen but not to the pathogen itself. It can lead to multiorgan failure if inadequately treated. Nearly all patients with cytokine storm are febrile, and the fever may be high grade in severe cases. In addition, patients may have fatigue, anorexia, headache, rash, diarrhea, arthralgia, myalgia, and neuropsychiatric findings.

Patients with severe COVID-19 are at high risk for occlusion of blood vessels of all sizes. This prothrombotic phenotype is reminiscent of patients with lupus and antiphospholipid syndrome, who have long-lived circulating antiphospholipid autoantibodies. In new work, Zuo et al. measured eight types of antiphospholipid antibodies in serum from patients hospitalized with COVID-19 and found at least one antibody in half of patients. Antibody levels were associated with neutrophil and coagulation pathway activation. Purified antibodies from some patients activated neutrophils in vitro and potentiated thrombosis when injected into mice. Together, these findings suggest that autoantibodies are a potential therapeutic target in severe COVID-19.

Critically ill patients with coronavirus disease 2019 (COVID-19) have a profound hypercoagulable state and often develop thrombosis in veins, arteries and in the microcirculation. COVID-19 is a thrombotic disorder in large part because more than half of hospitalized COVID-19 patients have positive antiphospholipid (aPL) antibodies. Hunt, a world-renowned expert in thrombosis from the UK, said she had "never seen such sticky blood as is present in COVID-19". Now the aPL issue is complicating the Johnson & Johnson COVID vaccine, the Johnson & Johnson vaccinations having been halted across the country after the emergence of a few clotting cases.

Under one or more preferred embodiments of the present invention, given that low-level full body UV-A1 exposures can decrease or eliminate antiphospholipid antibodies, a UV-A1 irradiation treatment process and therapy of the present invention can be used against thrombosis and its sequelae in COVID-19. The elevated aCL antibodies in COVID-19 could become a major reason for using full body low-dose, UV-A1 irradiation routinely in COVID-19 patients. These are the same antibodies physicians find in patients with an autoimmune disease called antiphospholipid syndrome, in which antibodies seed clots by attracting clotting factors that eventually block blood flow.

Aside from its antioxidant capacity, HO-1 has anticoagulant properties, including fibrinolysis, protective in the prothrombotic milieu of COVID-19. The HO-1 product CO inhibits platelet aggregation by activating guanylate cyclase (GC). HO-1 and its products, CO and bilirubin inhibit thrombus formation. CO represses the fibrinolytic axis, and is anti-inflammatory, in opposition to COVID-19 that is closely linked to inflammation.

The HO system acts as a potent antioxidant, protecting endothelial cells from apoptosis, while maintaining vascular tone, increasing angiogenesis, reducing endothelial inflammation and apoptosis and stoking angiogenesis and vasculogenesis.

HO-1, Pregnancy and COVID-19

Pregnant people with COVID-19 are at an increased risk for severe illness from COVID-19, including illness that results in Intensive Care Unit (ICU) admission, mechanical ventilation, and death-compared with non-pregnant people. Additionally, pregnant people with COVID-19 might be at increased risk for other adverse outcomes, such as preterm birth. Emerging evidence supports an important role for the heme oxygenase system in the maintenance of a healthy pregnancy. HO-1 is present normally but can also be triggered by UV-A1 photons. It is an important regulator of placental development, important in pregnancy and preeclampsia, particularly in its vascular structure.

The HO protein and more specifically its catalytic by-products (CO, biliverdin, and Fe2+) have been postulated to be involved in the maintenance of uterine quiescence throughout gestation, regulation of hemodynamic control within the uterus and placenta, regulation of the apoptotic and inflammatory cascades in trophoblast cells, and maintenance of the balance of the oxidant-antioxidant status within the placental tissues. HO-1 aids placental development by decreasing the oxidative stress; it promotes an immune tolerant microenvironment at the fetal-maternal interface. CO, a downstream product of HO-1, has been implicated in maintaining vascular tone, increasing angiogenesis, and reducing inflammation and apoptosis.

Recent data suggests that induction of the HO-1 system or administration of its bioactive metabolites, provides a promising novel therapeutic approach to the management of pregnancy during COVID-19 infection. UV-A1 irradiation of one or more preferred embodiments of the present invention can supplant this system.

CORM

HO-1 products can be used individually, such as CO, through the inhalation of the CO gas or through implantation of a CO-releasing molecule (CORM). Although this can bring about some of the protective advantages of HO-1, including its likely aid in prevention of and recovery from COVID-19 infection and damage, the use of CORM is risky, invasive, exacting, and may require added expenses such as hospitalization, cumbersome gas cylinder transport and storage and a need for protection against non-patient exposure. Far better is low dose, UV-A1 photon irradiation pursuant to one or more preferred embodiments of the present invention. It is a safe, convenient and physiologic means of activating HO-1 and its products. Under one or more preferred embodiments of the present invention, several (e.g., about 2 to 3 days per week, about 20 to 30 minute exposures, for about 2 to 4 weeks or longer as needed to UV-A1 full body irradiation at 6 to 15 $J/cm^2$) exposures to UV-A1 light can be used instead of CORM. Under one or more preferred embodiments of the present invention, several (e.g., about 2 to 3 days per week, about 20 to 30 minute exposures, for about 2 to 3 months or longer as needed to UV-A1 full body irradiation at 6 to 8 $J/cm^2$) exposures to UV-A1 light can be used instead of CORM. In other preferred embodiments, several (e.g., about 2 to 3 days per week, about 20 to 30 minute exposures, for about 2 to 3 months or longer as may be needed to UV-A1 full body irradiation at 7 to 15 $J/cm^2$) exposures to UV-A1 light can be used instead of CORM.

Metabolic Syndrome

HO-1 also downregulates hypertension, hyperlipidemia, diabetes, obesity, and atherosclerosis, i.e. metabolic syndrome, a central exacerbator of COVID-19. Bilirubin, which is produced from HO-1-generated biliverdin, is negatively associated with hemoglobin A1C levels, metabolic syndrome, and insulin resistance. HO-1, generated by whole body UV-A1 irradiation under one or more preferred embodiments of the present invention down regulates metabolic syndrome, a central exacerbator of COVID-19. Obesity, hypercholesterolemia, and atherosclerotic heart disease are associated with more severe COVID-19 presentations. The anti-hypertensive effects of UVA radiation may be dependent on the release of nitric oxide from preformed skin stores. Under one or more preferred embodiments of the present invention, several (e.g., about 2 to 3 days per week, about 20 to 30 minute exposures, for about 2 to 4 weeks or longer as needed to UV-A1 full body irradiation at 6 to 15 $J/cm^2$) exposures to UV-A1 light can be used to help alleviate these conditions or symptoms. Under one or more preferred embodiments of the present invention, several (e.g., about 2 to 3 days per week, about 20 to 30 minute exposures, for about 2 to 3 months or longer as needed to UV-A1 full body irradiation at 6 to 8 $J/cm^2$) exposures to UV-A1 light can be used to help alleviate these conditions or symptoms. In other preferred embodiments, several (e.g., about 2 to 3 days per week, about 20 to 30 minute exposures, for about 2 to 3 months or longer as may be needed to UV-A1 full body irradiation at 7 to 15 $J/cm^2$) exposures to UV-A1 light can be used to help alleviate these conditions or symptoms.

Cigarettes, Admissions, Increased HO-1, CO Anti-Viral, and Anesthetics

A recent observation that fewer cigarette-smokers are admitted with COVID-19 compared with non-smokers may be explained by the high level of CO in smoke. The CO released by HO-1 and by smoking suppresses inflammation. CO is both viricidal and anti-inflammatory. Cigarette smoke, which, like UV-A1 photon irradiation, raises levels of HO-1, and even more, CO. In China, current smokers had ¼th the prevalence of COVID-19 hospitalizations as the general population and in France, the smoker rate was 5% of COVID-19 admissions compared with a 25% smoker rate for the general French population. Relevantly, cigarette smoke is associated with increased HO-1 induction in lung fibroblasts and vascular endothelial cells. To restate, as a major factor released from the catalytic action of HO-1 on heme, CO is anti-inflammatory, anti-oxidative and anti-viral.

Animals for Testing

Animals are available for testing the action of UV-A1 irradiation on COVID-19, but as proven with SLE treatments, it is safe for use in humans.

Other UV-A1 Effects

Other indications that UV-A1 photons can have beneficial systemic actions lies in its disease-reversing potential in pulmonary hypertension (PH), interstitial lung disease (ILD), sub-acute lupus erythematosus (SCLE), discoid lupus erythematosus (DLE), anti-phospholipid antibody syndrome (aPS), and lupus-related central nervous system disease. These actions of total body low dose UV-A1 irradiation support this beneficial impact in disease.

In one or more preferred embodiments of the present invention, UV-A1 photon irradiation may offer a supplemental means of protecting against infection with a mutant of COVID-19 or in eliminating signs and symptoms reported to linger after resolution of the active infection. Under one or more preferred embodiments of the present invention, several (e.g., about 2 to 3 days per week, about 20 to 30 minute exposures, for about 2 to 4 weeks or longer as needed to UV-A1 full body irradiation at 6 to 15 $J/cm^2$) exposures to UV-A1 light can be used to help alleviate these conditions or symptoms. Under one or more preferred embodiments of the present invention, several (e.g., about 2 to 3 days per week, about 20 to 30 minute exposures, for about 2 to 3 months or longer as needed to UV-A1 full body irradiation at 6 to 8 $J/cm^2$) exposures to UV-A1 light can be used to help alleviate these conditions or symptoms. In other preferred embodiments, several (e.g., about 2 to 3 days per week, about 20 to 30 minute exposures, for about 2 to 3 months or longer as may be needed to UV-A1 full body irradiation at 7 to 15 $J/cm^2$) exposures to UV-A1 light can be used to help alleviate these conditions or symptoms.

Neurologic Disease in COVID-19

Recent studies have found the novel coronavirus in the brains of fatal cases of COVID-19. It has been suggested that infection of olfactory neurons in the nose may be all that enable the virus to spread from the respiratory tract to the brain. Under one or more preferred embodiments of the present invention, several (e.g., about 2 to 3 days per week, about 20 to 30 minute exposures, for about 2 to 4 weeks or longer as needed to UV-A1 full body irradiation at 6 to 15 J/cm$^2$) exposures to UV-A1 light would be all that would be needed to work against this progression. Under one or more preferred embodiments of the present invention, several (e.g., about 2 to 3 days per week, about 20 to 30 minute exposures, for about 2 to 3 months or longer as needed to UV-A1 full body irradiation at 6 to 8 J/cm$^2$) exposures to UV-A1 light would be all that would be needed to work against this progression. In other preferred embodiments, several (e.g., about 2 to 3 days per week, about 20 to 30 minute exposures, for about 2 to 3 months or longer as may be needed to UV-A1 full body irradiation at 7 to 15 J/cm$^2$) exposures to UV-A1 light would be all that would be needed to work against this progression.

Oral and nasal epithelial cell ACE-2 facilitates nasopharyngeal entry and at times, entry to the brain. There is a unique CNS presentation, brain fatigue, a symptom originally described in SLE, and responding remarkably to the full body, low-dose UV-A1 irradiation. Taste and smell may be next followed by inability to taste, muscle weakness, tingling or numbness in the hands and feet, dizziness, confusion, delirium, seizures, and stroke. Nationwide, a small number of people who have recovered from COVID-19 are reporting neurological concerns such as headache, dizziness, lingering loss of smell or taste, muscle weakness, nerve damage, and trouble thinking or concentrating. This latter sometimes called "COVID fog" or "brain fog" is a cognitive dysfunction presenting as decreased attentiveness, memory deficits, diminished problem-solving capability, and decreases in information organization. This was often the symptom complex most immediately, striking, and gratifyingly eliminated by UV-A1 irradiation therapy in patients with SLE. One or two full body, 20-minute (6 J/cm$^2$) exposures to full-body UV-A1 photon irradiation in patients with SLE was telling and can be used to treat COVID-19 patients as well in one or more preferred embodiments of the present invention. In SLE it was the harbinger of a wider response, as it might be in COVID-19. Due primarily to the HO-1 product, CO, other lingering post-COVID-19 CNS symptoms most likely may be similarly responsive.

HO-1 exhibits other neuroprotective effects through the anti-inflammatory, anti-apoptotic and vasodilatory properties of CO. In concert with nitric oxide (NO), CO binds to and activates soluble guanylate cyclase (sGC), a heme-containing protein that mediates smooth muscle relaxation, inhibits inflammation, and abrogates ischemic insult to neuronal cells. It decreases the propensity for thrombosis and cerebral vasospasm, pathology observed in the HO-1-deficient mouse. In addition to modulating cerebral vascular resistance, the combination of sGC and GMP enhances neurotransmission and improves learning and memory, which are commonly impaired in patients with SLE and improved by UV-A1 irradiation. Brain fog responds to full body low dose UV-A1 therapy in SLE and is a common symptom in COVID-19.

COVID-19 is responsible early-on for the central nervous system symptoms of headaches, dizziness, loss of taste and smell and impaired consciousness. These are most common in patients with severe disease. The neuroprotective actions of HO-1 are mimicked by application of the CO-releasing molecule CORM 2, meaning that the HO-1 protection is due for the most part to its HO-1 catalytic product, CO.

Short Term Memory

Patients during and for a short period after COVID-19 infection struggle with short-term memory. Patients complain, for instance, that they walk to the kitchen and forget what they were looking for. Multitasking is impossible. It takes them longer to get things done, and they often feel confused and overwhelmed. Some patients struggle to return to work or to school. Under one or more preferred embodiments of the present invention, several (e.g., about 2 to 3 days per week, about 20 to 30 minute exposures, for about 2 to 3 months or longer as needed to UV-A1 full body irradiation at 6 to 8 J/cm$^2$) exposures to UV-A1 light can be used to treat or combat short term memory issues. In other preferred embodiments, several (e.g., about 2 to 3 days per week, about 20 to 30 minute exposures, for about 2 to 3 months or longer as may be needed to UV-A1 full body irradiation at 7 to 15 J/cm$^2$) exposures to UV-A1 light can also be used to treat or combat short term memory issues. Under one or more preferred embodiments of the present invention, several (e.g., about 2 to 3 days per week, about 20 to 30 minute exposures, for about 2 to 4 weeks or longer as needed to UV-A1 full body irradiation at 6 to 15 J/cm$^2$) exposures to UV-A1 light can also be used to treat or combat short term memory issues.

Guillain-Barré Syndrome

COVID-19 may cause Guillain-Barre syndrome or neurological disorders akin to it, due to neuroinflammation. Patients complain, for instance, that they walk to the kitchen and forget what they were looking for. Under one or more preferred embodiments of the present invention, several (e.g., about 2 to 3 days per week, about 20 to 30 minute exposures, for about 2 to 3 months or longer as may be needed to UV-A1 full body irradiation at 6 to 8 J/cm$^2$) exposures to UV-A1 light can be used to treat or combat Guillain-Barre syndrome or neurological disorders akin to it, due to neuroinflammation. In other preferred embodiments, several (e.g., about 2 to 3 days per week, about 20 to 30 minute exposures, for about 2 to 3 months or longer as may be needed to UV-A1 full body irradiation at 7 to 15 J/cm$^2$) exposures to UV-A1 light can also be used to treat or combat Guillain-Barre syndrome or neurological disorders akin to it, due to neuroinflammation. In other preferred embodiments, several (e.g., about 2 to 3 days per week, about 20 to 30 minute exposures, for about 2 to 4 weeks or longer as may be needed to UV-A1 full body irradiation at 6 to 15 J/cm$^2$) exposures to UV-A1 light can also be used to treat or combat Guillain-Barre syndrome or neurological disorders akin to it, due to neuroinflammation.

Alzheimer's and Parkinson's Disease

The novel coronavirus pandemic has seen a surge in Alzheimer's disease and deaths from related dementias, in which 15,000 more Americans have died from dementias than in the same time frame in past years. CO, released by HO-1, acts as a "chemical messenger" in the brain, helping nerve cells to communicate with each other. Moreover, the CO-donor CORM-2 protects cells against the beta amyloid peptide in Alzheimer's disease strongly suggesting that singlet oxygen activation of HO-1 may provide the same relief through the release of CO, a molecule that improves mitochondrial biogenesis and counteracts NADPH oxidase-induced ROS generation. Under one or more preferred embodiments of the present invention, several (e.g., about 2 to 3 days per week about 20 to 30 minute exposures for about 2 to 3 months or longer as may be needed to UV-A1 full body irradiation at 6 to 8 J/cm$^2$) exposures to UV-A1 light can be used to combat Alzheimer's disease and symptoms. In other preferred embodiments, several (e.g., about 2 to 3 days per week about 20 to 30 minute exposures for about 2 to 3 months or longer as may be needed to UV-A1 full body irradiation at 7 to 15 J/cm$^2$) exposures to UV-A1 light can also be used to combat Alzheimer's disease and symptoms. In other preferred embodiments, several (e.g., about 2 to 3 days per week about 20 to 30 minute exposures for about 2 to 4 weeks or longer as may be needed to UV-A1 full body irradiation at 6 to 15 J/cm$^2$) exposures to UV-A1 light can also be used to combat Alzheimer's disease and symptoms.

As to Parkinson disease, seniors are the most vulnerable to COVID-19 and to Parkinson disease (PD). Oxidative stress is implicated and heme oxygenase-1 (HO-1) a potent antioxidant. Under one or more preferred embodiments of the present invention, several (e.g., about 2 to 3 days per week, about 20 to 30 minute exposures, for about 2 to 3 months to UV-A1 full body irradiation at 6 to 8 J/cm$^2$) exposures to UV-A1 light can be used to combat Parkinson disease and symptoms. In other preferred embodiments, several (e.g., about 2 to 3 days per week, about 20 to 30 minute exposures, for about 2 to 3 months or longer as may be needed to UV-A1 full body irradiation at 7 to 15 J/cm$^2$) exposures to UV-A1 light can also be used to combat Parkinson disease and symptoms. In other preferred embodiments, several (e.g., about 2 to 3 days per week, about 20 to 30 minute exposures, for about 2 to 4 weeks or longer as may be needed to UV-A1 full body irradiation at 6 to 15 J/cm$^2$) exposures to UV-A1 light can also be used to combat Parkinson disease and symptoms.

Virus-Induced Encephalitis/CO

The SARS-CoV-2-induced immunologic responses, e.g., cytokine storm, may cause inflammatory injury and edema, resulting in alterations in consciousness. With the clearance of virus, the CSF pressure gradually decreases, and the patient's consciousness gradually improves. It is the HO-1 product CO once again that down-modulates this oxidant immune response and its associated inflammation. Under one or more preferred embodiments of the present invention, several (e.g., about 2 to 3 days per week, about 20 to 30 minute exposures, for about 2 to 3 months or longer as may be needed to UV-A1 full body irradiation at 6 to 8 J/cm$^2$) exposures to UV-A1 light can be used to combat such cytokine storm. In other preferred embodiments, several (e.g., about 2 to 3 days per week, about 20 to 30 minute exposures, for about 2 to 3 months or longer as may be needed to UV-A1 full body irradiation at 7 to 15 J/cm$^2$) exposures to UV-A1 light can also be used to treat or combat such cytokine storm. In other preferred embodiments, several (e.g., about 2 to 3 days per week, about 20 to 30 minute exposures, for about 2 to 4 weeks or longer as may be needed to UV-A1 full body irradiation at 6 to 15 J/cm$^2$) exposures to UV-A1 light can also be used to treat or combat such cytokine storm.

Vestibular Neuritis

Vestibular neuritis has been reported in COVID-19. In several reports, healthy young people with a very strong response to COVID-19 suffered Guillain-Barré syndrome (acute inflammatory demyelinating polyneuritis), COVID-19 encephalitis, and stroke, these young people having otherwise mild systemic COVID-19 symptoms. Under one or more preferred embodiments of the present invention, several (e.g., about 2 to 3 days per week, about 20 to 30 minute exposures, for about 2 to 3 months or longer as may be needed to UV-A1 full body irradiation at 6 to 8 J/cm$^2$) exposures to UV-A1 light can be used to treat Vestibular neuritis and symptoms, Guillain-Barré syndrome and encephalitis symptoms. In other preferred embodiments, several (e.g., about 2 to 3 days per week, about 20 to 30 minute exposures, for about 2 to 3 months or longer as may be needed to UV-A1 full body irradiation at 7 to 15 J/cm$^2$) exposures to UV-A1 light can also be used to treat Vestibular neuritis and symptoms, Guillain-Barré syndrome and encephalitis and symptoms. In other preferred embodiments, several (e.g., about 2 to 3 days per week, about 20 to 30 minute exposures, for about 2 to 4 weeks or longer as may be needed to UV-A1 full body irradiation at 6 to 15 J/cm$^2$) exposures to UV-A1 light can also be used to treat Vestibular neuritis and symptoms, Guillain-Barré syndrome and encephalitis symptoms.

UV-A1 irradiation of the present invention as shown and described herein can also be used to potentially help with future viral pandemics, which may include those due to more virulent viruses for which a vaccine has not yet been developed. UV-A1 radiation may kill viruses more indiscriminately than vaccines, so its usefulness will target those intervals when a new vaccine is needed or being developed. The delivery systems, e.g., irradiators, e.g., sunbeds of preferred embodiments of the present invention can be readily procured.

In one or more preferred embodiments, of the present invention, any potential inconvenience of employing a UV-A1 sunbed for COVID-19 disease is offset by the comfort, safety and high impact of UV-A1 irradiation as a gentle and effective anti-Covid-19 ordnance. The therapeutic effectiveness of UV-A1 in SLE has opened the door for testing its effectiveness in a variety of diseases.

In one or more preferred embodiments of the present invention, a light bulb can include a filter as part of the light bulb as a first step to blocking light other than UV-A1 light. Another filter can be added to such a light bulb to further block light except for UV-A1 light that is desired to be blocked. For example, a TL/10R Philips lamp, e.g., a TL 100W/10-R UV-A or PHILIPS TL 80W/10-R includes a filter and this light bulb can also be covered by another filter, e.g., a Mutzhas UVASUN-pink filter or Polycast™ QT 2730-1 filter, to help ensure that pure UV-A1 photons are emitted for use in the treatment of patients.

A filter that can be used in the present invention can be made of acrylic, or a flexible plastic material that can preferably be wrapped around a bulb and can filter out harmful UV light.

A filter of the present invention that can filter out light except for desired light, e.g., desired light being UV-A1 light and possibly visible light, can also be obtained from Polycast™ company.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 8 is a partial view of a lamp/light that can be used in one or more preferred embodiments of the therapy, treatment and process of the present invention;

FIG. 9 is a perspective view of a filter that can be included on a lamp/light in one or more preferred embodiments of the therapy, treatment and process of the present invention;

FIG. 10 is a partial cut-away view of lamp/light with a filter that can be used in one or more preferred embodiments of the therapy, treatment and process of the present invention;

DETAILED DESCRIPTION OF THE INVENTION

Figure 1:
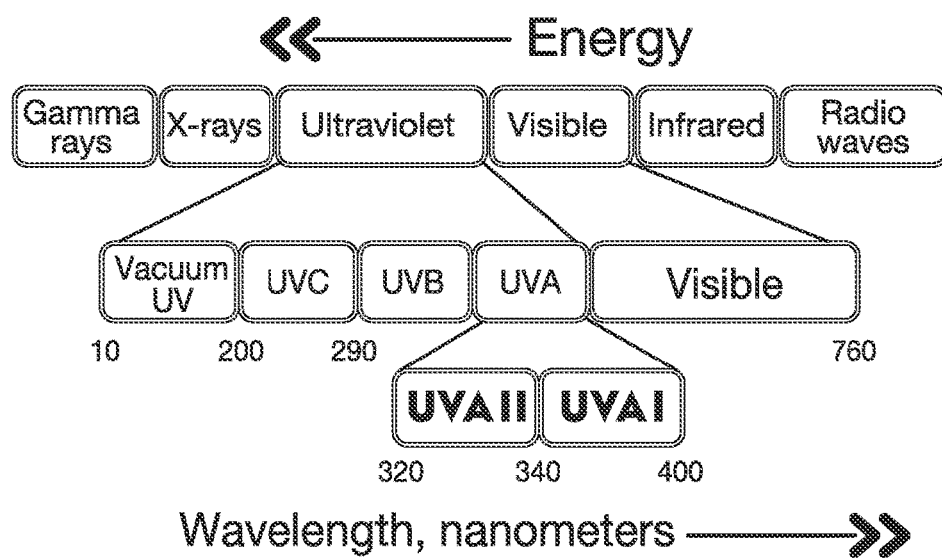
FIG. 1 is a chart that illustrates UV-A1 light as part of the ultraviolet spectrum.
Figure 3:
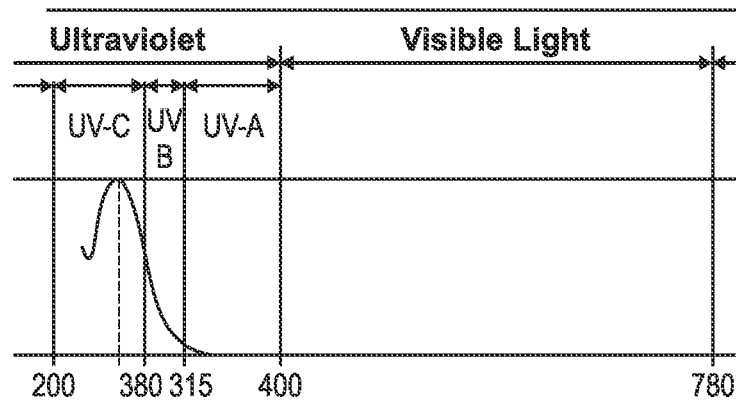
FIG. 3 is a chart that illustrates the electromagnetic light spectrum including ultraviolet light and visible light.
Figure 4:
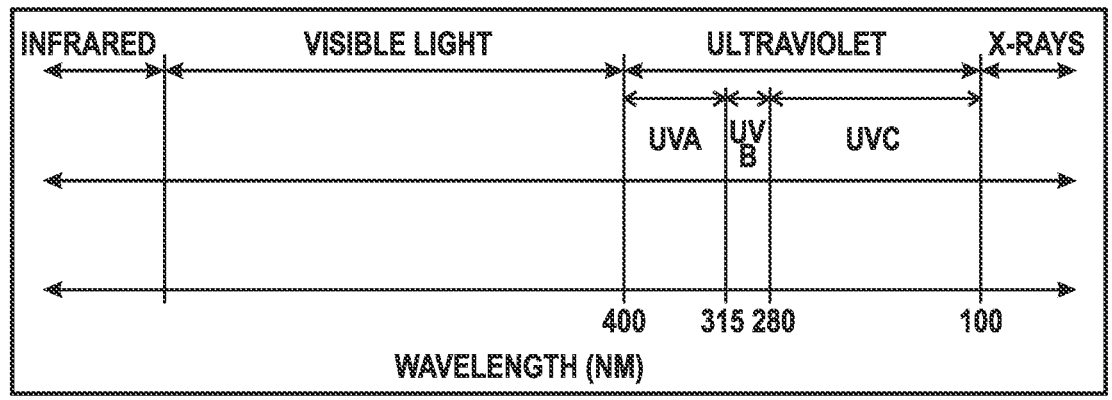
FIG. 4 is a chart that illustrates the electromagnetic light spectrum.

As shown in FIG. 1, 3-4 ultraviolet (UV) radiation is part of the electromagnetic spectrum, encompassing wavelengths between X-rays (0.01 to 10 nm) and visible light (390 to 700 nm), the UV divided into ultraviolet A (UV-A; 320-400 nm) and ultraviolet B (UV-B; 280-320 nm). The UV-A band is further subdivided into ultraviolet-A2 (UV-A2; 320-340 nm) having properties close to those of UV-B, and ultraviolet-A1 (UV-A1; 340-400 nm) with properties more closely related to those of visible light.

Figure 2:
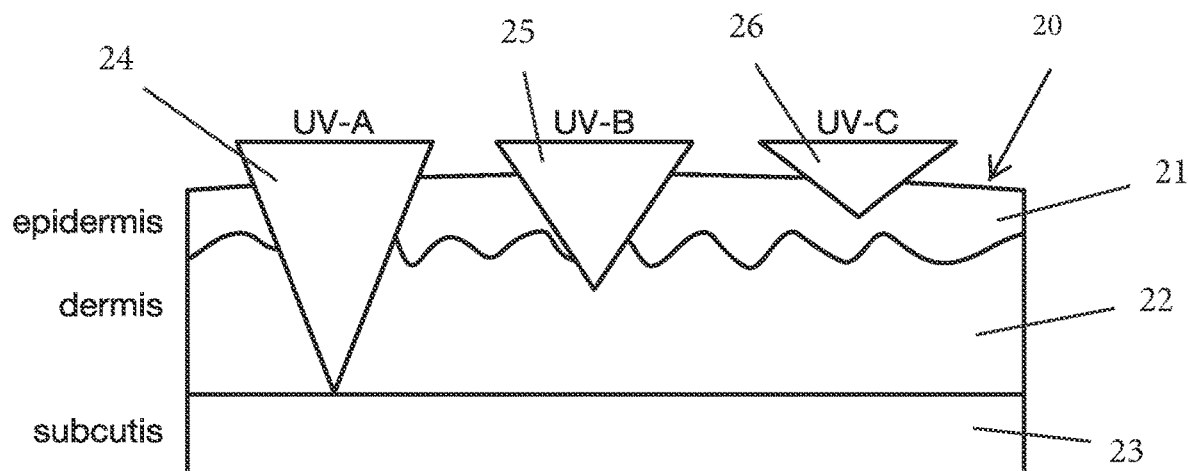
FIG. 2 is a diagram that illustrates UV-A1 photon penetration in human skin wherein it easily penetrates the epidermis and upper dermis to reach the sub dermis where it reaches the vasculature with its circulating cells and also reaches infiltrating cells such as tissue macrophages.

UV-B wavelengths (depicted by triangle 25 in FIG. 2), damaging to the skin, cause sunburn. They are absorbed by deoxyribonucleic acid (DNA) and therefore penetrate little further than the epidermis 21 of human skin 20. UV-C wavelengths (depicted by triangle 26 in FIG. 2) also penetrate only the epidermis 21. UV-A1 wavelengths (depicted by triangle 24 in FIG. 2), on the other hand, the longest, most abundant, lowest in energy, and deepest penetrating of all the UV wavelengths reach photoreceptors in the dermis 22, such as those on infiltrating dermal macrophages, and reach the subdermal vasculature with its circulating cells, giving the sub dermis a wide systemic reach for the UV-A1 photons. The subcutis 23 is also depicted in FIG. 2.

UV-A1 photons are the only known exogenously delivered activators of singlet oxygen ($^1O_2$), an electronically excited form of molecular oxygen and primary mediator of UV-A1 photon action. UV-A1 wavelengths were isolated in 1981 with the use of Mutzhas-pink filters (Radiation apparatus: patent number 4,298,005 Nov. 3, 1981). In 1986 using TL/10R Philips lamps (Philips International, Eindoven, The Netherlands), covered by the Mutzhas-pink filters, pure UV-A1 photons were emitted for use in the treatment of patients with SLE.

The UV wavelengths make up the portion of the electromagnetic spectrum between X-rays (0.01 to 10 nm) and visible (390 to 700 nm) light (FIG. 1). They are conventionally divided into ultraviolet A, (UV-A; 320-400 nm), ultraviolet B (UV-B 280-320 nm) and ultraviolet C (UVC; 200-280 nm). The UV-A band is further subdivided into UV-A2 (320-340 nm) having properties close to those of UV-B (280-320 nm) and UV-A1 (340-400 nm) the longest band of UV wavelengths, whose properties are close to those of visible light. 340 nm is generally considered part of the UV-A2 and UV-A1 wavelength range; 340 nm is considered part of the UV-A1 spectrum in one or more embodiments of the treatment and process described and/or claimed herein.

UV-A1 photons penetrate the skin in a wavelength dependent manner, the longest wavelengths penetrating most deeply. During exposure to broad spectrum UV, approximately 100 times more UVA than UVB photons reach the dermis. UV-A1 wavelengths comprise 75% of the UVA band. The isolated UV-A1 wavelengths emitted by a UV-A1 lamp of the present invention reach deeply, into and beyond the dermis, giving them the widest systemic reach of all the UV wavelengths. They are absorbed as far as the sub dermis, along the way reaching infiltrating macrophages and cells circulating in the dermal and subdermal capillaries. UV-B wavelengths by contrast are absorbed by DNA epidermal keratinocyte DNA only 10% reaching the dermis. UV-B is dermal whereas UV-A1 acts systemically.

The UV-A1 photon energy absorbed by photosensitizers within cells, is transferred to oxygen, raising this diatomic molecule to its electronically excited state, $^1O_2$. $^1O_2$ has physical properties that distinguish it from the more prevalent triplet ground state oxygen. As a highly reactive ROS, $^1O_2$ readily oxidizes a variety of biological molecules and becomes a primary mediator of UV-A1 photon action.

$^1O_2$, an electrophile, activates Nrf2, a governor of antioxidant forces, to act through HO-1 to reverse cell injury. HO-1 peaks during anticipated injury, such as with the ischemic reactivity that comes with heart surgery, or following hyperoxygenation after high level oxygen therapy. The supplemental HO-1 generated by UV-A1 exposures can be released in anticipation of an injury which the body's own HO-1 system cannot do, as it activates only after an injury.

UV-A1 irradiation is dermal but has systemic effect because its photons increase HO-1 expression in the dermis and sub-dermis for as long as three days. This affords time for the added burst of HO-1 and its products to act, both locally and in distant tissues. It also means that the HO-1 actions can be maintained by continued UV-A1 exposures, e.g., 2-4 times a week to extend their remedial action. The HO-1 gene can also be transferred by adenovirus vector, a far more complicated and risky approach. Administration of any of the HO-1 products individually, such as CO through CO inhalation or the implantation of a CO-releasing molecule (CO-RM), can increase the effectiveness of the particular effect, as desired. However, these too are risky, invasive, exacting, and expensive techniques. Inhaled CO, for example, sometimes requires hospitalization, cumbersome gas cylinder transport and storage and a need for protection against non-patient exposure. Full-body, low dose, UV-A1 photon irradiation is safe, convenient, comfortable and physiologic as a means of activating HO-1 systemically, availing patients of all the downstream products of HO-1, i.e., CO, BV, and BR.

In one or more preferred embodiments of the present invention, a low-dose of UV-A1 irradiation can be 6 to 8 $J/cm^2$. Other doses can also be used, e.g., 8 J to 15 $J/cm^2$.

In one or more preferred embodiments of the present invention, a low-dose or a dose of UV-A1 is selected for administering to a patient that will cause no more than a light tan to the skin of the patient.

In one or more preferred embodiments of a phototherapy treatment and process for a patient suffering from a Corona virus, e.g., COVID-19, includes the following steps:

using an irradiator to treat COVID-19 by subjecting a patient's full body to UV-A1 light having a wavelength between 360 to 400 nm at (8-10 J/cm$^2$/day) for about 20 to 30 minutes for about 3 to 4 days per week for about 3 to 4 weeks or more as may be needed.

In one or more preferred embodiments of a phototherapy treatment and process for a patient suffering from a Corona virus, e.g., COVID-19, includes the following steps:

using an irradiator to treat COVID-19 by subjecting a patient's full body to UV-A1 light having a wavelength between 360 to 400 nm at (8-10 J/cm$^2$/day) for about 20 to 30 minutes for about 2 to 3 days per week for about 3 to 4 weeks or more as may be needed.

In one or more preferred embodiments of a phototherapy treatment and process for a patient suffering from a Corona virus, e.g., COVID-19, includes the following steps:

using an irradiator to treat COVID-19 by subjecting a patient's body to UV-A1 light having a wavelength between 360 to 400 nm at (8-10 J/cm$^2$/day) for about 20 to 30 minutes for about 3 to 4 days per week for about 3 to 4 weeks or more as may be needed.

In one or more preferred embodiments of a phototherapy treatment and process for a patient suffering from a Corona virus, e.g., COVID-19, includes the following steps:

using an irradiator to treat COVID-19 by subjecting a patient's body to UV-A1 light having a wavelength between 360 to 400 nm at 8-10 J/cm$^2$/day for about 20 to 30 minutes for about 2 to 3 days per week for about 3 to 4 weeks or more as may be needed.

In one or more preferred embodiments of a phototherapy treatment and process for a patient suffering from a Corona virus, e.g., COVID-19, includes the following steps:

using an irradiator to treat COVID-19 by subjecting a patient's body to UV-A1 light having a wavelength between 360 to 400 nm at 6-15 J/cm$^2$/day for about 20 to 30 minutes for about 2 to 4 days per week for about 3 to 4 weeks or more as may be needed.

In other embodiments, 340 to 350 nm can also potentially be used but may cause some sunburn and may have fewer of the beneficial $^1O_2$ effects as this range is closer to the UV-B range.

In one or more preferred embodiments, the same or similar UV-A1 treatment process used to treat COVID-19 as shown and/or described herein can also be used to treat other Corona viruses, other viruses, secondary illnesses or conditions or side effects caused by COVID-19 or another virus, and/or some pre-existing conditions or illnesses of patient's who have a virus, some examples of which are discussed further herein.

A 360 to 400 nm dose at 8-10 J/cm$^2$/day is well below the sunburn level. Most patients may experience no more than a light tan, especially if they are lightly pigmented. Active disease during the 3 to 4 days and 3 to 4 weeks, or desired treatment time, can be measured by viral and antibody levels. The UV-A1 irradiation will trigger the production of singlet oxygen, an anti-viral. Singlet oxygen additionally in turn, activates the gene for heme oxygenase (HO-1), an enzyme that produces carbon monoxide, which inhibits respiratory viruses.

A Philips lamp covered by the Mutzhas filters is able to emit 360-400 nm of UV-A1 and can be used in one or more preferred embodiments of the present invention.

In other preferred embodiments, different lamps and/or filters can be used in the treatment of COVID-19 or other corona viruses or other viruses that are capable of transmitting 340 to 400 nm light. Preferably a filter is used with a lamp of the present invention when it is desired or necessary to filter out wavelengths that can potentially be, or are, harmful to a person, e.g., wavelengths of the UVB and UVA-2, range, while allowing wavelengths of the UVA-A1 range to be transmitted.

Figure 5:
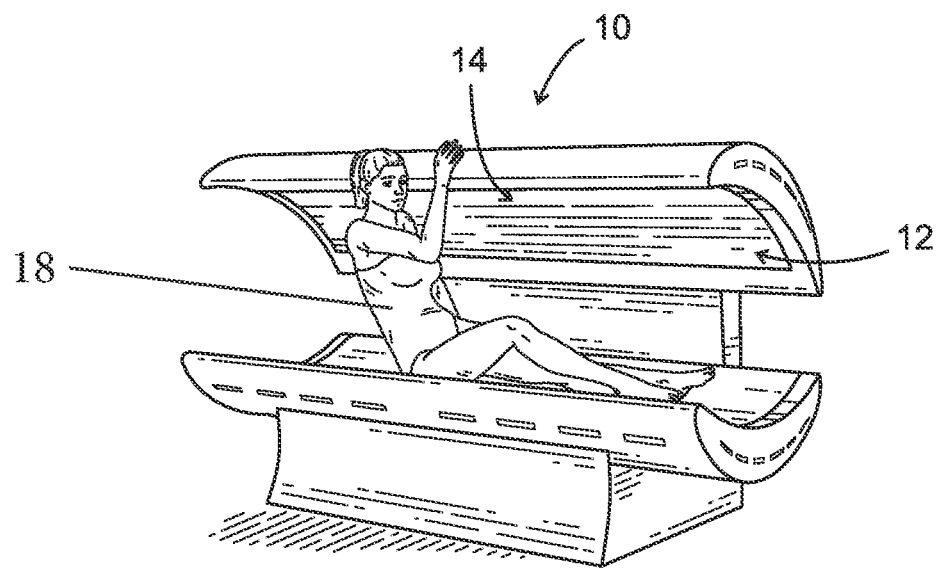
FIG. 5 is a perspective view of an irradiator that can be used in one or more preferred embodiments of the therapy, treatment and process of the present invention.
Figure 6:
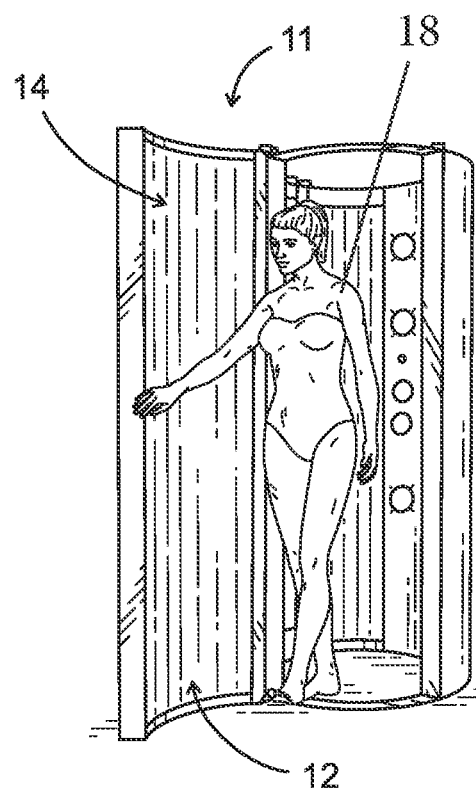
FIG. 6 is a perspective view of another irradiator that can be used in one or more preferred embodiments of the therapy, treatment and process of the present invention.
Figure 7:
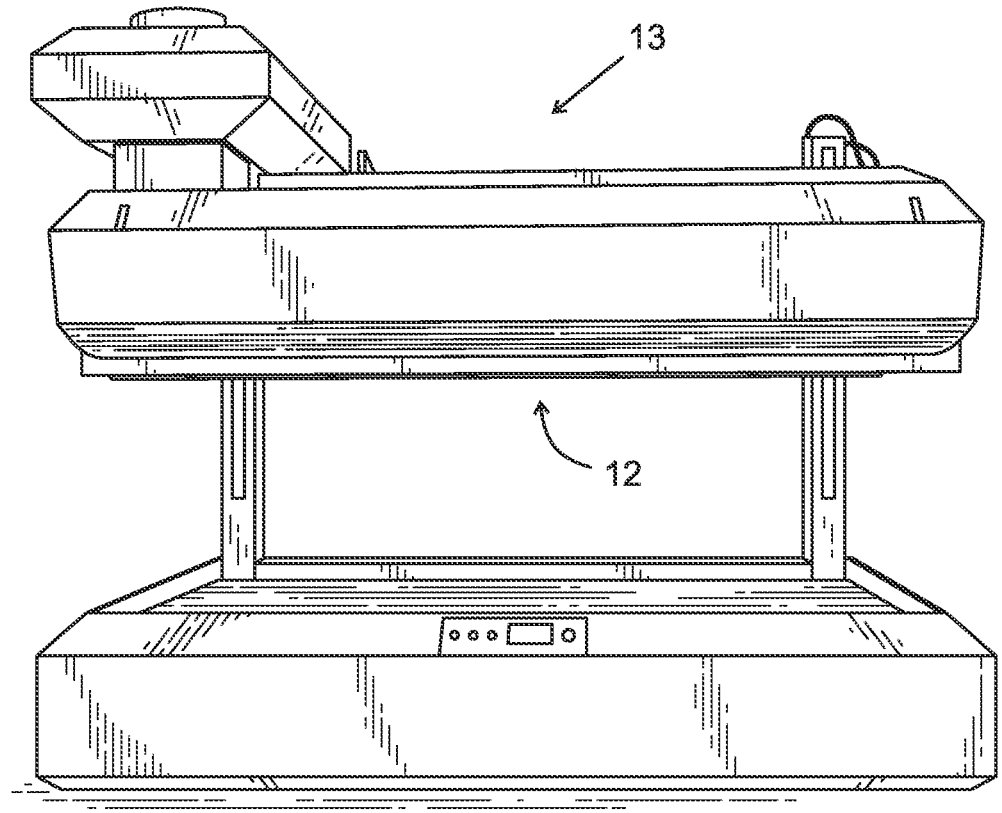
FIG. 7 is a perspective view of another irradiator that can be used in one or more preferred embodiments of the therapy, treatment and process of the present invention.

FIGS. 5-7 illustrate examples of irradiators 10, 11, 13 that can be used in one or more preferred embodiments of a phototherapy of the present invention, e.g., a sunbed available from Phillips or AliSun or SunFire manufacturers. Irradiator 10 as shown in FIG. 5 is a bench and canopy type. As seen in FIG. 5, a patient 18 can lie within irradiator 10 and be exposed to full body UV-A1 light. Irradiator 11 is of the type adapted to allow a person 18 to stand within the irradiator 11 and be exposed to full body UV-A1 light, which can be used in one or more preferred embodiments of the present invention. FIG. 7 shows another embodiment of an irradiator 13 in a which a patient's body can also be exposed to UV-A1 light in one or more preferred embodiments of the present invention. Other irradiator sun beds and standing chambers available on the market can also be used in the present invention that includes a lamps, and preferably a filter, that is capable of transmitting 340 to 400 nm light.

Each irradiator can include UV-A1 light bulbs 12, e.g., Philips TL/10R UV-A1 sunlamps (Philips company, Eindhoven, the Netherlands). Preferably the UV-A1 light bulbs 12 include a filter 14 that allows UV-A1 light having wavelengths of 340 to 400 nm to be emitted, while at least substantially filtering out other light, including, e.g., higher energy solar wavelengths of ultraviolet A2 (UV-A2, 320 to 339 nm) and ultraviolet-B (UV-B, 280-320 nm). An example of a filter 14 that can be used in one or more preferred embodiments is Mutzhas UVASUN filters Mutzhas filters (Mutzhas Company, Munich Germany) which preferably cover light bulbs 12. A Polycast™ QT 2730-1 filter can also be a filter 14. This Philips TL/10R UV-A1 sunlamps lamp/ Mutzhas UVASUN filter duo allows emission of UV-A1 photons, excluding all others. This maximizes the generation in cells of UV-A1-induced singlet oxygen and in combination with the cell's own intrinsic production of singlet oxygen, delivers $^1O_2$ at levels greater than by any other known means. Other UV-A1 light bulbs or sun lamps and filters that allow for UV-A1 light emission while excluding other desired light that are currently available on the market, or to be developed in the future, can also be used in the present invention.

FIG. 8 is a partial view of a light bulb/lamp 12 that can be used in an irradiator of one or more embodiments of the present invention. Light bulb/lamp 12 can have a socket 16 at each end with pins 17, for example, that can connect to a power source. Other type designs of a light bulb or socket can also be used if desired. FIG. 9 depicts a filter 14 that can be wrapped around light bulb 12, as shown in the partial cutaway view of FIG. 10.

Figure 11:
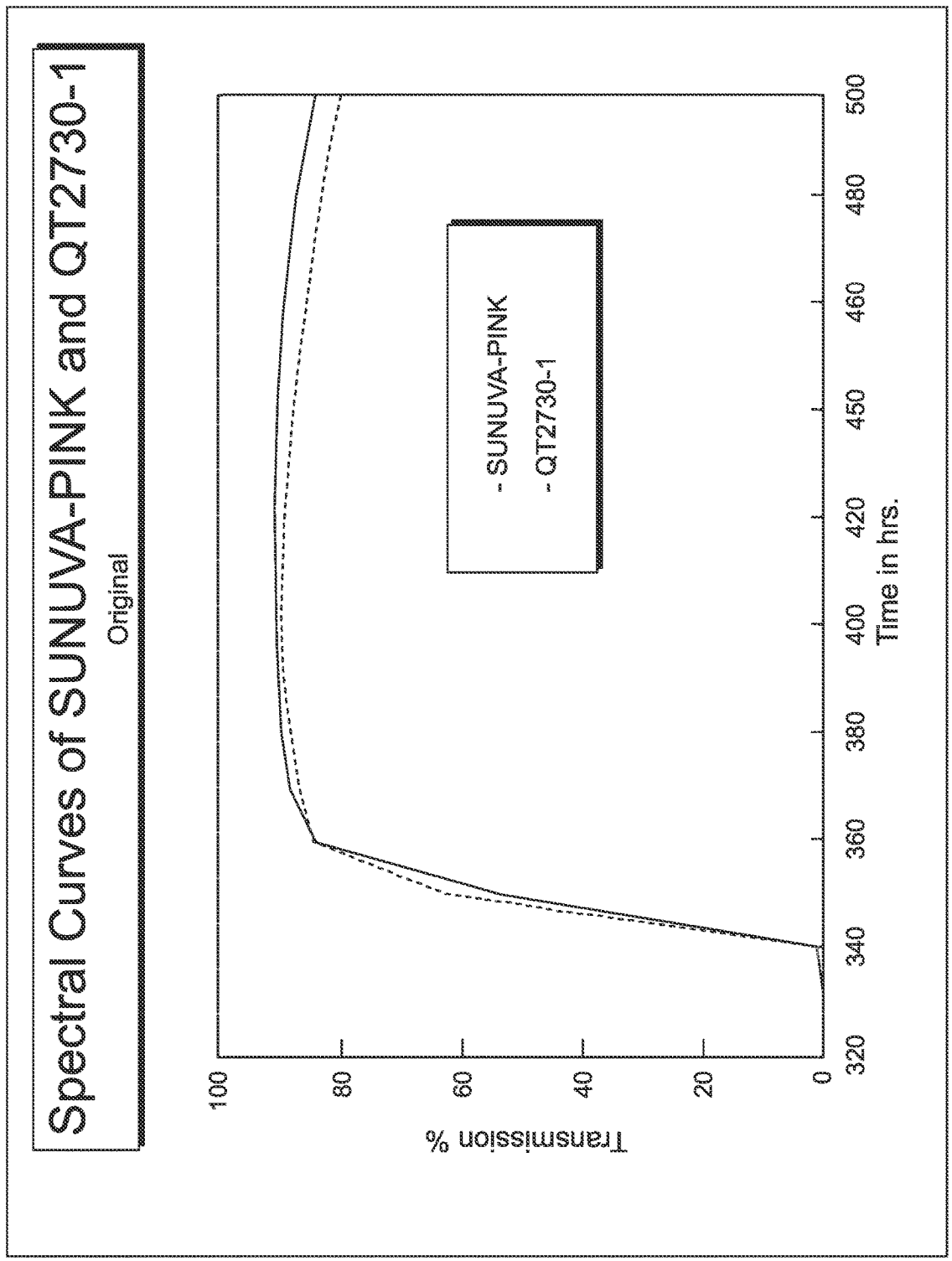
FIG. 11 is a graph illustrating spectral curves of SUNUVA-PINK and QT2730-1 filters.
Figure 12:
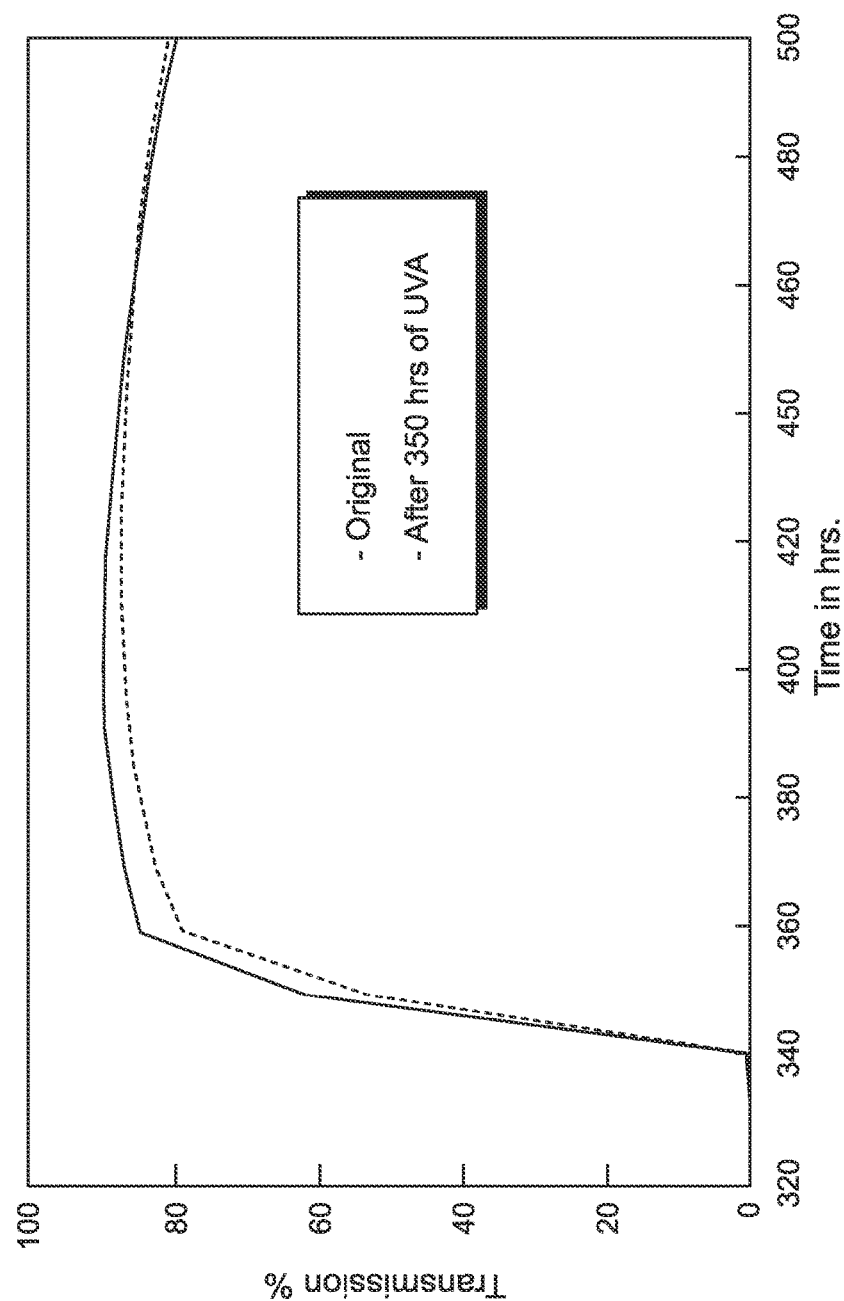
FIG. 12 is a graph illustrating spectral curves of a QT2730-1 filter.
Figure 13:
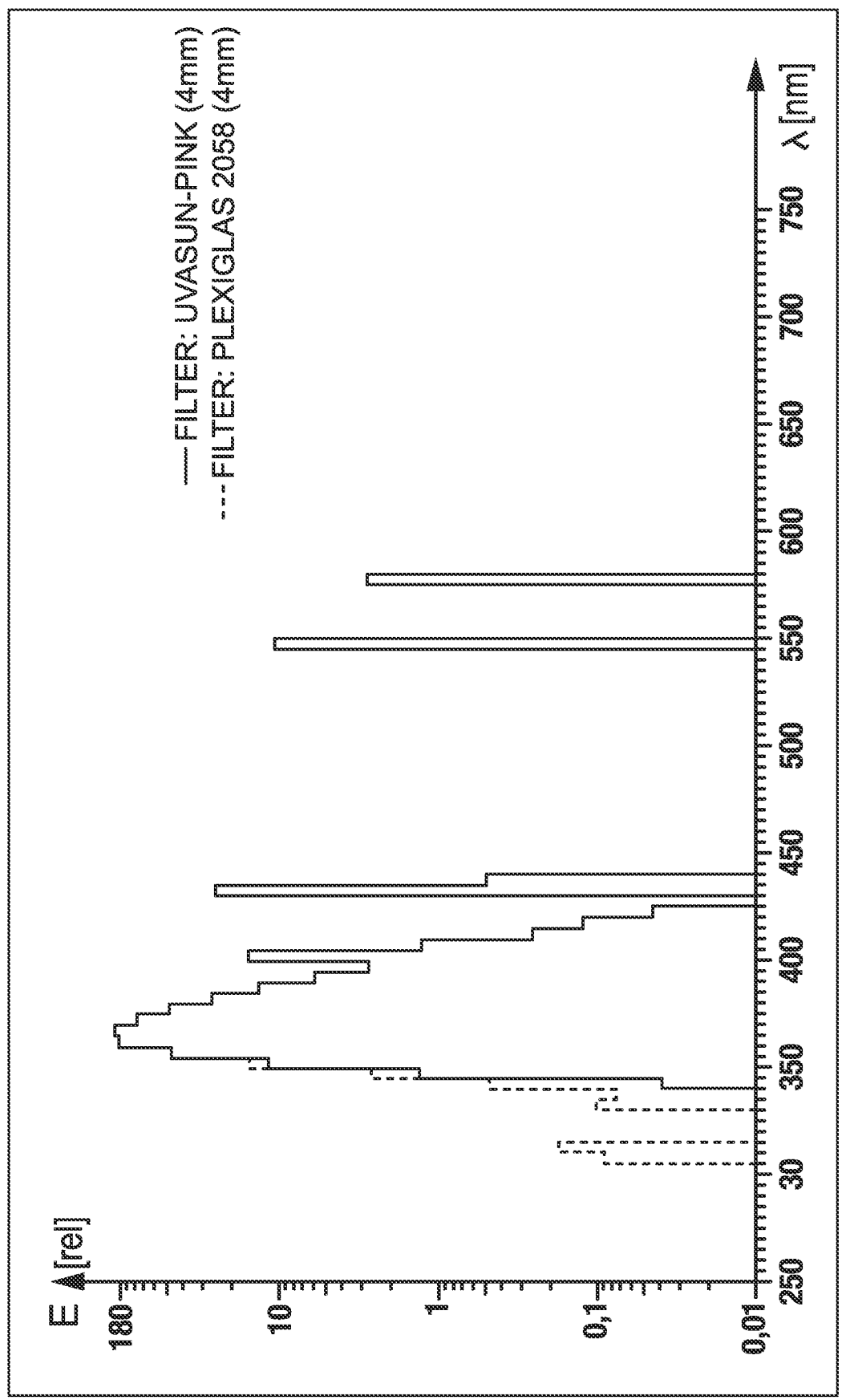
FIG. 13 is a graph illustrating spectral power distribution of filtered SUNUVA-PINK UV-A fluorescent lamp TL/10 compared to a plexiglass filter.

FIGS. 11-13 are charts illustrating the spectral curve of light of different filtering materials, e.g., UVASUN-Pink filter, QT2730-1 Polycast™ filter, and Plexiglas™.

In one or more embodiments, a filter 14 included for the light bulbs 12 can allow emission of UV-A1 light and visible light.

In one or more embodiments, a filter included for the light bulbs 12 can allow emission of UV-A1 light.

In one or more preferred embodiments, each irradiator 10, 11, 13 can be tuned to emit UV-A1 light at a specified wavelength, e.g., 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, or 420 nanometers, for a specified duration of time.

In one or more preferred embodiments, each irradiator 10, 11, 13 can be tuned to emit UV-A1 light at a desired specified range of wavelengths that is selected between 340 and 420 nm.

Regarding duration and timing of treatments and therapy, in one or more preferred embodiments, a patient can have at least two treatments a week for longer sessions, e.g., using 6-15 $J/cm^2$/day per session for two sessions per week for 30 to 40 minutes.

Regarding duration and timing of treatments and therapy, in one or more preferred embodiments, a patient can have at least two treatments a week for longer sessions, e.g., using 7-15 $J/cm^2$/day per session for two sessions per week for 30 to 40 minutes A patient also possibly could have one treatment per week, but the greater the number of treatments per week the more singlet oxygen that will be produced for more killing power towards COVID-19 or other corona viruses.

In one or more embodiments, treatments can be 2 to 4 times a week for 3 to 5 weeks, wherein the amount of treatments per patient and duration of the treatments can be determined based on a patient's antiviral levels as the treatments progress. For example, if a patient no longer tests positive for COVID-19, or another corona virus after one or two weeks of treatments, the treatment course can end.

In one or more embodiments, treatments can be 1 to 5 times a week for 1 to 5 weeks, wherein the amount of treatments per patient and duration of the treatments can be determined based on a patient's antiviral levels as the treatments progress. For example, if a patient no longer tests positive for COVID-19, or another corona virus after one or two weeks of treatments, the treatment course can end.

Treatments possibly can be daily during a week of treatment, but generally this is not necessary giving the duration of the systematic effect created by the UV-A1 treatment. Some testing has shown that there appears to be no added effect in exposing patient's to UV-A treatment more than 3 days per week.

Preferably a single therapy session is of long enough duration to produce sufficient levels of singlet oxygen to help inactive and/or kill COVID-19 or other corona viruses but is not too long so as to cause a sun burn on a patient's skin.

In one or more embodiments, a single therapy session can last up to 45 minutes, wherein the longer the session the more potential for suntan to occur.

In one or more embodiments, a single therapy session can last up to 40 to 45 minutes.

In one or more embodiments, a single therapy session can last 10 to 20 minutes.

In one or more embodiments, more than one therapy session can be between 10 to 45 minutes, for example.

In one or more embodiments, more than one therapy session can potentially be provided for a patient in a single day, with each therapy session between 10 to 20 minutes, for example.

In one or more preferred embodiments, more than one therapy session can potentially be provided for a patient in a single day, with each therapy session between 10 to 45 minutes, for example.

In one preferred embodiment, a method of treating a patient suffering from Corona Virus Disease 2019 (COVID-19), comprises the steps of:
(a) subjecting the patient's body to UV-A1 light having a wavelength between 360 to 400 nm at 8-10 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:
(a) subjecting the patient's body to UV-A1 light having a wavelength between 360 to 400 nm at 6-15 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:
(a) subjecting the patient's body to UV-A1 light having a wavelength between 360 to 400 nm at 7-10 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:
(a) subjecting the patient's body to UV-A1 light having a wavelength between 360 to 400 nm at 8-15 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:
(a) subjecting the patient's body to UV-A1 light having a wavelength between 360 to 400 nm at 6-15 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:
(a) subjecting the patient's body to UV-A1 light having a wavelength between 340 to 400 nm at 8-10 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:
(a) subjecting the patient's body to UV-A1 light having a wavelength between 340 to 400 nm at 6-15 J/cm2/day for a selected time interval and at multiple selected times;
(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:

(a) subjecting the patient's body to UV-A1 light having a wavelength between 340 to 400 nm at 7-10 J/cm2/day for a selected time interval and at multiple selected times;

(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:

(a) subjecting the patient's body to UV-A1 light having a wavelength between 340 to 400 nm at 8-15 J/cm2/day for a selected time interval and at multiple selected times;

(b) wherein step (a) includes emitting radiation from an irradiator lamp with a filter that allows emission of UV-A1 photons while at least substantially excluding other photons.

In one preferred embodiment, a method of treating a patient suffering from Corona Virus Disease 2019 (COVID-19), comprises the steps of:

(a) subjecting the patient's body to UV-A1 light having a wavelength between 340 to 400 nm at 6-15 J/cm2/day for a selected time interval and at multiple selected times;

(b) wherein step (a) includes emitting radiation from an irradiator lamp with a filter that allows emission of UV-A1 photons while at least substantially excluding other photons.

In a preferred embodiment a patient will not be on photosensitizing medication or using lotions or topical skin treatments that could cause a rash or adverse reaction under the UV-A1 light.

The therapy and treatment processes as disclosed herein can also be used to kill other viruses or bacteria that can be inactivated or killed by UV-A1 light.

In various preferred embodiments, a therapy relies on the UV-A1 irradiation production of singlet oxygen within a patient's body. The treatment apparatus, including a light filer, e.g., a Mutzhas™ filter atop a Philips™ UV-A1 lamp, emits a UV-A1 radiation more pure than exists anywhere known in the universe. As UV-A1 photons penetrate the skin deeply enough to reach the vasculature, (the blood), its effects, unlike those of all other UV wavelengths that are essentially only skin-deep, reach the entire body, through the blood so its effects can therefore be considered systemic rather than local.

Moreover, by eliminating the other UV wavelengths, UVC, UVB and UV-A2, the therapy eliminates the established inhibitory and dilutional effects of these other UV wavelengths on UV-A1 so the UV-A1 photons delivered to patients through the lamp/filter engine are delivered more pure and unobstructed than by any other means. As this UV-A1 engine generates enough singlet oxygen in vivo to reverse lupus activity, it is capable of also delivering enough singlet oxygen to kill Corona viruses in vivo, including COVID-19, as it does in vitro.

The following is a list of parts and materials suitable for use in the present invention:

PARTS LIST:

| PART NUMBER | DESCRIPTION |
|---|---|
| 10 | irradiator |
| 11 | irradiator |
| 12 | light bulb/lamp |
| 13 | irradiator |
| 14 | filter |
| 16 | socket |
| 17 | pin |

-continued

PARTS LIST:

| PART NUMBER | DESCRIPTION |
|---|---|
| 18 | patient/person |
| 20 | skin |
| 21 | epidermis |
| 22 | dermis/sub-dermis |
| 23 | subcutis |
| 24 | UV-A light |
| 25 | UV-B light |
| 26 | UV-C light |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A systemic phototherapy treatment and process for a patient suffering from Corona Virus Disease 2019 (COVID-19), comprising the following steps:
using an irradiator to systemically treat the COVID-19 by externally subjecting at least a substantial portion of a patient's body to a band of solar UV-A1 light having wavelengths of 340 to 400 nm at 6-15 J/cm$^2$/day for 20 to 30 minutes in 3 to 4 days per week for 3 to 4 weeks.

2. The phototherapy treatment of claim 1 wherein the UV-A1 light has a wavelength of 360 to 400 nm at 8-10 J/cm$^2$/day for 20 to 30 minutes for 3 to 4 days per week for 3 to 4 weeks and a patient's full body, excepting eyes and personal areas that are covered, is subjected to UV-A1 light.

3. The phototherapy treatment of claim 1 wherein the UV-A1 light has a wavelength of 340 to 400 nm at 6-10 J/cm$^2$/day, and is emitted for 20 to 30 minutes, for 3 to 4 days, for 2 to 4 weeks.

4. The phototherapy treatment of claim 1 wherein the UV-A1 light has a wavelength of 340 to 400 nm at 7-15 J/cm$^2$/day, emitted over a period of 20 to 30 minutes, 3 to 4 days a week, for 2 to 4 weeks.

5. The phototherapy treatment of claim 1 wherein the irradiator includes a bench and canopy.

6. The phototherapy treatment of claim 1 wherein the irradiator is adapted to allow a patient to stand within the irradiator.

7. The phototherapy treatment of claim 1 wherein the irradiator includes light bulbs that emit light having a wavelength of 340 to 400 nm, and the light bulbs are covered in a filter that blocks emission of harmful light.

8. The phototherapy treatment of claim 7, wherein the harmful light includes ultraviolet A2 (320-339 nm) and ultraviolet-B (280-320 nm).

9. The phototherapy treatment of claim 7 wherein the light bulbs are covered in a filter that blocks emission of UV-A2 light and UV-B light and UV-C light.

10. The phototherapy treatment of claim 7 wherein the filter allows emission of visible light such as blue light.

11. A method of treating a patient suffering from Corona Virus Disease 2019 (COVID-19), comprising the steps of:
(a) externally subjecting at least a substantial part of skin of the patient to a band of solar UV-A1 light having wavelengths between 340 to 400 nm at 8-10 J/cm$^2$/day for a selected time interval and at multiple selected times;

(b) wherein step (a) includes emitting radiation from an irradiator lamp with a filter that allows emission of UV-A1 photons while at least substantially excluding other photons;

wherein the band of solar UV-A1 light is absorbed as far as a sub dermis, along the way reaching infiltrating macrophages and cells circulating in dermal and sub-dermal capillaries where the UV-A1 light triggers production of singlet Oxygen, which activates a gene for heme oxygenase, which releases from heme carbon monoxide, biliverdin and bilirubin to target the COVID-19 and reduce inflammatory responses caused by the COVID-19.

12. The method of claim 11, wherein the time interval is between 20 and 30 minutes and the multiple selected times is for 3 to 4 days per week for 3 to 4 weeks.

13. The method of claim 11 wherein the UV-A1 light has a wavelength of 340 to 400 nm, and is emitted for 10-40 minutes, for 3 to 4 days, for 3 to 4 weeks.

14. The method of claim 11 wherein the UV-A1 light has a wavelength of 340 to 400 nm, and is emitted for 10 to 45 minutes, for 2 to 4 days, for 2 to 4 weeks.

15. The method of claim 11 wherein the irradiator lamp includes light bulbs that emit light having a wavelength of 340 to 400 nm, and the light bulbs are filtered with a filter that blocks emission of UV-A2 light, UV-B light, and UV-C light.

16. The method of claim 11 wherein the UV-A1 light has a wavelength of 340-400 nm at 6-15 J/cm$^2$/day, and is emitted for 10 to 45 minutes, for 1 to 5 days, for 1 to 5 weeks.

17. A systemic phototherapy treatment and process for alleviating one or more symptoms or side effects or secondary illnesses caused by Corona Virus Disease 2019 (COVID-19) including post COVID-19 conditions, for a patient who is suffering from COVID-19 or recovered from COVID-19, includes the following steps:

using an irradiator to treat the symptoms or secondary illnesses by subjecting at least a substantial portion of skin of the patient to a band of solar UV-A1 light having a plurality of wavelengths between 340 to 400 nm at 6-15 J/cm$^2$/day for 10 to 45 minutes for 1 to 5 days per week for 1 to 5 weeks or 1 to 3 months, wherein the band of solar UV-A1 light is absorbed as far as a sub dermis, along the way reaching infiltrating macrophages and cells circulating in dermal and sub-dermal capillaries where the UV-A1 light triggers production of singlet oxygen, which activates a gene for heme oxygenase, which produces carbon monoxide to target the COVID-19 and/or reduce inflammatory responses caused by the COVID-19 and other inflammatory conditions.

18. The phototherapy treatment and process of claim 17 wherein the symptom or secondary illness or pre-existing condition is acute respiratory distress syndrome, inflammation of lungs, cytokine storm syndrome, blood clots, hypercoagulation, thrombosis, or a metabolic syndrome.

19. The phototherapy treatment and process of claim 17 wherein the process can be used to help maintain a healthy pregnancy of the patient while or after suffering from COVID-19.

20. The phototherapy treatment and process of claim 17 wherein the symptom or secondary illness or pre-existing condition is a neurologic disease, Alzheimer's disease, Parkinson's disease, short-term memory, Guillain Barre syndrome, neuroinflammation, or vestibular neuritis.

* * * * *